(12) United States Patent
Smyth et al.

(10) Patent No.: US 6,649,596 B1
(45) Date of Patent: *Nov. 18, 2003

(54) MODIFIED VEGF OLIGONUCLEOTIDES FOR INHIBITION OF TUMOR GROWTH

(75) Inventors: Adrienne P. Smyth, Charlton, MA (US); Gregory S. Robinson, Acton, MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/124,304

(22) Filed: Jul. 29, 1998

Related U.S. Application Data

(63) Continuation-in-part of application No. 08/629,730, filed on Apr. 9, 1996, now abandoned, which is a continuation-in-part of application No. 08/569,926, filed on Dec. 8, 1995, now Pat. No. 5,641,756.

(51) Int. Cl.[7] ............... C07H 21/04; C21N 15/85; C21N 15/86; C12Q 1/68; A61K 48/00
(52) U.S. Cl. ............... 514/44; 536/24.5; 435/6; 435/325; 435/375
(58) Field of Search ............... 514/44; 435/6, 435/91.1, 91.3, 325, 375; 536/23.1, 24.5, 23.2, 24.3, 24.31, 24.33

(56) References Cited

U.S. PATENT DOCUMENTS 5,585,479 A * 12/1996 Hoke et al. ............... 536/24.5

OTHER PUBLICATIONS

Gewirtz et al. "Facilitating oligonucleotide delivery: Helping antisense deliver on its promise", Proc Natl. Acad. Sci., vol 93, p 3161–316, Apr. 1996.*
Rojanasakul, "Antisense oligonucleotide therapeutics: drug dlivery and targeting", Advanced Drug Delivery Reviews vol 18, p 115–131, 1996.*
Branch, "A good antisense molecule is hard to find", TIBS 23, p 45–50, Feb. 1998.*

* cited by examiner

Primary Examiner—Karen Lacourciere
(74) Attorney, Agent, or Firm—Hale and Dorr LLP

(57) ABSTRACT

Disclosed are oligonucleotides complementary to VEGF-specific nucleic acid useful in reducing the expression of VEGF. Also disclosed are pharmaceutical formulations containing such oligonucleotides useful for treating various disorders associated with neovascularization and angiogenesis.

8 Claims, 9 Drawing Sheets

```
         90                                    58           OLIGO   SEQ. ID#
    -GGCTCCAATGCACCCAAGACAGCAGAAAGTTCATGGT-5'   TARGET   21
           5' ─────────────────────────▶ 3'     H3        1
              ──────────────────────────▶       H3Ia      2
              ────────────────────────▶         H3-I      3
              ──────────────────────────▶       H3-Ja     4
              ────────────────────────▶         H3-J      5
              ──────────────────────────────▶   H3-Xa     6
              ────────────────────────────▶     H3-X      7
              ──────────────────────────────▶   H3-Ya     8
              ────────────────────────────▶     H3-Y      9
              ──────────────────────────────▶   H3-Za    10
              ────────────────────────────▶     H3-Z     11
                    ──────────────────▶         H3-D     12
                    ────────────────▶           H-3E     13
                      ────────────▶             H-3F     14
                      ──────────────▶           H-3G     15
                        ────────────▶           H-3H     16
```

MODIFIED VEGF OLIGONUCLEOTIDES FOR INHIBITION OF TUMOR GROWTH

CROSS-REFERENCE TO RELATED APPLICATIONS

This application is a continuation-in-part of U.S. patent application Ser. No. 08/629,730, entitled "MODIFIED VEGF OLIGONUCLEOTIDES FOR THE TREATMENT OF SKIN DISORDERS," filed Apr. 9, 1996 (abandoned), which is a continuation-in-part of U.S. patent application Ser. No. 08/569,926, entitled "MODIFIED VEGF OLIGONUCLEOTIDES," filed Dec. 8, 1995 (U.S. Pat. No. 5,641,756).

BACKGROUND OF THE INVENTION

This invention relates to vascular endothelial growth factor. More specifically, this invention relates to oligonucleotides specific for vascular endothelial growth factor nucleic acid and useful treatment of disorders that are associated with neovascularization and angiogenesis, such as psoriasis.

Neovascular diseases of the retina such as diabetic retinopathy, retinopathy of prematurity, and age-related macular degeneration are a major cause of blindness in the United States and the world, yet the biochemical events responsible for these processes have not been fully elucidated.

Diabetic retinopathy is the leading cause of blindness among working age adults (20–64) in the United States (Foster in *Harrison's Principles of Internal Medicine* (Isselbacher et al., eds.) McGraw-Hill, Inc., New York (1994) pp. 1994–1995). During the course of diabetes mellitus, the retinal vessels undergo changes that result in not only leaky vessels but also vessel drop out resulting in retinal hypoxia. The effects of these complications are hemorrhaging, "cotton wool" spots, retinal infarcts, and neovascularization of the retina resulting in bleeding and retinal detachment. If left untreated, there is a 60% chance of visual loss. Classic treatment for proliferative diabetic retinopathy is panretinal laser photocoagulation (PRP). However, complications can occur from panretinal laser photocoagulation such as foveal burns, hemorrhaging, retinal detachment, and choroidal vessel growth. Furthermore, other untoward effects of this treatment are decreased peripheral vision, decreased night vision, and changes in color perception (*Am. J. Ophthamol.* (1976) 81:383–396; *Ophthalmol.* (1991) 98:741–840). Thus, there is a need for a more effective treatment for diabetic retinopathy.

Retinopathy of prematurity (ROP) is a common cause of blindness in children in the United States (Pierce et al. (1994) *Int. Ophth. Clinics* 34:121–148). Premature babies are exposed to hyperoxic conditions after birth even without supplemental oxygen because the partial pressure of oxygen in utero is much lower than what is achieved when breathing normal room air. This relative hyperoxia is necessary for their survival yet can result in ROP. The blood vessels of the retina cease to develop into the peripheral retina resulting in ischemia and localized hypoxic conditions as the metabolic demands of the developing retina increase. The resulting hypoxia stimulates the subsequent neovascularization of the retina. This neovascularization usually regresses but can lead to irreversible vision loss. There are at least 10,000 new-cases per year with a worldwide estimate of 10 million total cases. At present, there is no effective cure for ROP. Two therapeutic methods, cryotherapy and laser therapy, have been used but are not completely effective and themselves cause damage to the eye, resulting in a reduction of vision (Pierce et al. (1994) *Int. Ophth. Clinics* 34:121–148). Many other antiangiogenic compounds have been tested, but no inhibition in retinal neovascularization has been reported (Smith et al. (1994) *Invest. Ophthamol. Vis. Sci.* 35:1442; Foley et al. (1994) *Invest. Ophthamol. Vis. Sci.* 35:1442). Thus, there is a need for an effective treatment for ROP.

Age related macular degeneration is one of the leading causes of blindness in older adults in the United States, and may account for up to 30% of all bilateral blindness among Caucasian Americans (Anonymous (1994) *Prevent Blindness America*). This disease is characterized by loss of central vision, usually in both eyes, due to damage to retinal pigment epithelial cells which provide physiological support to the light sensitive photoreceptor cells of the retina. In most cases there is currently no effective treatment. In approximately 20% of exudative cases that are diagnosed early, laser treatment can prevent further loss of vision; however, this effect is temporary (Bressler et al., *Principles and Practices of Ophthamology* (eds. Albert and Jakobiac), W.B. Saunders Co., Philadelphia, Pa.) (1994) Vol. 2 pp. 834–852). Thus, there is a need for a more effective and permanent treatment for age related macular degeneration.

Ocular neovascularization is also the underlying pathology in sickle cell retinopathy, neovascular glaucoma, retinal vein occlusion, and other hypoxic diseases. These eye diseases as well as other pathological states associated with neovascularization (i.e., tumor growth, wound healing) appear to have hypoxia as a common factor (Knighton et al. (1983) *Science* 221:1283–1285; Folkman et al. (1987) *Science* 235:442–446; Klagsbrun et al. (1991) *Ann. Rev. Physiol.* 53:217–239; Miller et al. (1993) *Principles and Practice of Ophthamology*, W.B. Saunders, Philadelphia, pp. 760; and Aiello et al. (1994) *New Eng. J. Med.* 331:1480–1487). Moreover, retinal neovascularization has been hypothesized to be the result of a "vasoformative factor" which is released by the retina in response to hypoxia (Michaelson (1948) *Trans. Ophthamol. Soc. U. K.* 68:137–180; and Ashton et al. (1954) *Br. J. Ophthamol.* 38:397–432). Recent experimental data show a high correlation between vascular endothelial growth factor expression and retinal neovascularization (Aiello et al. (1994) *New Eng. J. Med.* 331:1480–1487). Furthermore, elevated levels of vascular endothelial growth factor have recently been found in vitreous from patients with diabetes (Aiello et al., ibid.). Thus, this cytokine/growth factor may play an important role in neovascularization-related disease.

Vascular endothelial growth factor/vascular permeability factor (VEGF/VPF) is an endothelial cell-specific mitogen which supports angiogenesis in wound healing and development. In addition, VEGF has recently been shown to be stimulated by hypoxia and required for tumor angiogenesis (Senger et al. (1986) *Cancer* 46:5629–5632; Kim et al. (1993) *Nature* 362:841–844; Schweiki et al. (1992) *Nature* 359:843–845; Plate et al. (1992) *Nature* 359:845–848). It is a 34–43 kD (with the predominant species at about 45 kD) dimeric, disulfide-linked glycoprotein synthesized and secreted by a variety of tumor and normal cells. In addition, cultured human retinal cells such as pigment epithelial cells and pericytes have been demonstrated to secrete VEGF and to increase VEGF gene expression in response to hypoxia (Adamis et al. (1993) *Biochem. Biophys. Res. Commun.* 193:631–638; Plouet et al. (1992) *Invest. Ophthamol. Vis. Sci.* 34:900; Adamis et al. (1993) *Invest. Ophthamol. Vis. Sci.* 34:1440; Aiello et al. (1994) *Invest. Ophthamol. Vis. Sci.* 35:1868; Simorre-Pinatel et al. (1994) *Invest. Ophthamol. Vis. Sci.* 35:3393–3400). In contrast, VEGF in normal tissues is relatively low.

VEGF has also been shown to play a major role in other diseases associated with the aberrant angiogenesis, including tumor development and skin disorders. Conditions associated with such irregularities include cancer, rheumatoid arthritis, the bullous diseases (including bullous pemphigoid, dermatitis herpetiformis, and erythema multiforme), and psoriasis.

Psoriasis is a chronic skin disorder that affects one in fifty people world wide and over five million people in the United States. Approximately 150,000 to 250,000 new cases of psoriasis are diagnosed each year. Ten percent of people with psoriasis develop psoriatic arthritis. The most common form of the disease is called plaque psoriasis or psoriasis vulgaris. Other forms are pustular, guttate, inverse, and erythrodermic psoriasis.

The cause of psoriasis is unknown. The skin lesions of psoriasis vulgaris are in part a result of an excessive rapid growth and turnover of keratinocytes. Current types of treatment achieve some temporary relief (e.g., steroids, anthralin, calcipotriene, coal tar with or without light therapy, psoralen with UVA treatment, methotrexate, retinoids with or without UV light, and cyclosporin A). However, harmful side effects of these treatments exist which vary in degree of health hazard, and some must be carefully monitored by a physician. Furthermore most of these treatments result in a recurrence of the psoriasic symptoms.

Ballaun et al. (*J. Invest. Dermatol.* (1995) 104:7–10) have shown that the three major splice forms of VEGF are produced by human epidermal keratinocytes and can be detected in the supernatant of cell cultures. In addition, VEGF upregulation has been observed in bullous pemphigoid, dermatitis herpetiformis, and erythema multiforme (Brown et al. (1995) *J. Invest Dermatol.* 104:744–749). Furthermore, psoriasic lesions express elevated levels of transforming growth factor alpha (TGFα), a known inducer of VEGF in cell culture (Detmar et al. (*J. Invest. Dermatol.* (1995) 105:44–50), and VEGF levels of normal epidermal keratinocytes can be induced in response to elevated levels of TGFα.

Thus, VEGF appears to play a principle role in many pathological states and processes related to angiogenesis and neovascularization. Regulation of VEGF expression in tissues affected by the various conditions described above could therefore be key in treatment or preventative therapies associated with such disorders.

New chemotherapeutic agents termed "antisense oligonucleotides" have been developed which are capable of modulating cellular and foreign gene expression (see, Zamecnik et al. (1978) *Proc. Natl. Acad. Sci.* (USA) 75:280–284). Without being limited to any theory or mechanism, it is generally believed that the activity of antisense oligonucleotides depends on the binding of the oligonucleotide to the target nucleic acid (e.g. to at least a portion of a genomic region, gene or mRNA transcript thereof), thus disrupting the function of the target, either by hybridization arrest or by destruction of target RNA by RNase H (the ability to activate RNase H when hybridized to RNA).

VEGF-specific antisense oligonucleotides have been developed (Uchida et al. (1995) *Antisense Res. & Dev.* 5(1):87 (Abstract OP-10); Nomura et al., (1995) *Antisense Res. & Dev.* 5(1):91 (Abstract OP-18)), although none have been demonstrated to reverse neovascularization or angiogenesis. Thus, a need still remains for the development of oligonucleotides that are capable of reducing VEGF expression, and ultimately, of inhibiting the onset of diseases and disorders associated with the expression of VEGF.

SUMMARY OF THE INVENTION

It is known that cells affected by hypoxia induce VEGF, and that aberrant expression of VEGF has been observed in skin diseases characterized by neoangiogenesis and epidermal alterations. The present invention provides novel synthetic oligonucleotides specific for nucleotides 58 to 90 of the VEGF gene which can reduce the hypoxia- or TGFα-induced expression of VEGF mRNA and protein. This information has been exploited to develop the present invention which includes VEGF-specific oligonucleotides, pharmaceutical formulations, and methods of reducing the expression of VEGF mRNA and protein and of treating various diseases characterized by the over-expression of VEGF.

In one aspect, the invention provides a synthetic oligonucleotide complementary to a nucleic acid specific for human vascular endothelial growth factor. This oligonucleotide has a nucleic acid sequence set forth in the Sequence Listing as SEQ ID NOS:1–16.

As used herein, the term "synthetic oligonucleotide" refers to chemically synthesized polymers of nucleotides covalently attached via at least one 5' to 3' internucleotide linkage. In some embodiments, these oligonucleotides contain at least one deoxyribonucleotide, ribonucleotide, or both deoxyribonucleotides and ribonucleotides. In another embodiment, the synthetic oligonucleotides used in the methods of the invention are from about 15 to about 30 nucleotides in length. In preferred embodiments, these oligonucleotides contain from about 16 to 29 nucleotides.

For purposes of the invention, the term "oligonucleotide sequence that is complementary to a genomic region or an RNA molecule transcribed therefrom" is intended to mean an oligonucleotide that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, causing pseudoknot formation. Binding by Watson-Crick or Hoogsteen base pairing under physiological conditions is measured as a practical matter by observing interference with the function of the nucleic acid sequence.

In some embodiments, the synthetic oligonucleotide of the invention are modified in a number of ways without compromising their ability to hybridize to nucleotide sequences contained within the mRNA for VEGF. The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. In some preferred embodiments, at least one internucleotide linkage of the oligonucleotide is an alkylphosphonate, phosphorothioate, phosphorodithioate, phosphate ester, alkylphosphonothioate, phosphoramidate, carbamate, carbonate, phosphate triester, acetamidate, and/or carboxymethyl ester.

The term "modified oligonucleotide" also encompasses oligonucleotides having at least one nucleotide with a modified base and/or sugar, such as a 2'-O-substituted ribonucleotide. For purposes of the invention, the term "2'-O-substituted" means substitution of the 2' position of the pentose moiety with an —O— lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. In some embodiments the oligonucleotides of the invention include four or five ribonucleotides 2'-O-alkylated at their 5' terminus (i.e., 5' 2-O-alkylated ribonucleotides), and/or four or five ribonucleotides 2'-O-alkylated at their 3' terminus (i.e., 3' 2-O-alkylated ribonucleotides). In preferred embodiments, the nucleotides of the synthetic oligonucleotides are linked by a or at least one phosphorothioate internucleotide linkage. The phosphorothioate linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051–1054).

In another aspect, the invention provides a method of inhibiting VEGF expression. In this method, nucleic acid specific for VEGF is contacted with an oligonucleotide of the invention. As used herein, the term "nucleic acid" encompasses a genomic region or an RNA molecule transcribed therefrom. In some embodiments, the nucleic acid is mRNA.

Without being limited to any theory or mechanism, it is generally believed that the activity of oligonucleotides used in accordance with this invention depends on the hybridization of the oligonucleotide to the target nucleic acid (e.g. to at least a portion of a genomic region, gene or mRNA transcript thereof), thus disrupting the function of the target. Such hybridization under physiological conditions is measured as a practical matter by observing interference with the function of the nucleic acid sequence. Thus, a preferred oligonucleotide used in accordance with the invention is capable of forming a stable duplex (or triplex in the Hoogsteen pairing mechanism) with the target nucleic acid; activate RNase H thereby causing effective destruction of the target RNA molecule, and in addition is capable of resisting nucleolytic degradation (e.g. endonuclease and exonuclease activity) in vivo. A number of the modifications to oligonucleotides described above and others which are known in the art specifically and successfully address each of these preferred characteristics.

Also provided by the present invention is a pharmaceutical composition comprising at least one synthetic oligonucleotide of claim 1 in a physiologically acceptable carrier.

Another aspect of the invention includes pharmaceutical compositions capable of inhibiting neovascularization and thus are useful in the methods of the invention. These compositions include a synthetic oligonucleotide of the present invention which specifically inhibits the expression of vascular endothelial growth factor and a physiologically and/or pharmaceutically acceptable carrier.

The term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism.

Another aspect of the invention is assessment of the role of VEGF in neovascularization and angiogenesis associated with normal development and in various disease states.

Yet another aspect is a method of treating psoriasis by administering to a human afflicted with the disorder a therapeutically-affective amount of an oligonucleotide of the invention.

The subject oligonucleotides and methods of the invention also provide a means of examining the function of the VEGF gene in a cell, or in a control mammal and in a mammal afflicted with a neovascularization-related or psoriasis-related disorder. The cell or mammal is administered the oligonucleotide, and the expression of VEGF mRNA or protein and/or proteins which are known to interact with CDK4 is examined. Presently, gene function is often examined by the arduous task of making a "knock out" animal such as a mouse. This task is difficult, time-consuming and cannot be accomplished for genes essential to animal development since the "knock out" would produce a lethal phenotype. The present invention overcomes the shortcomings of this model.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
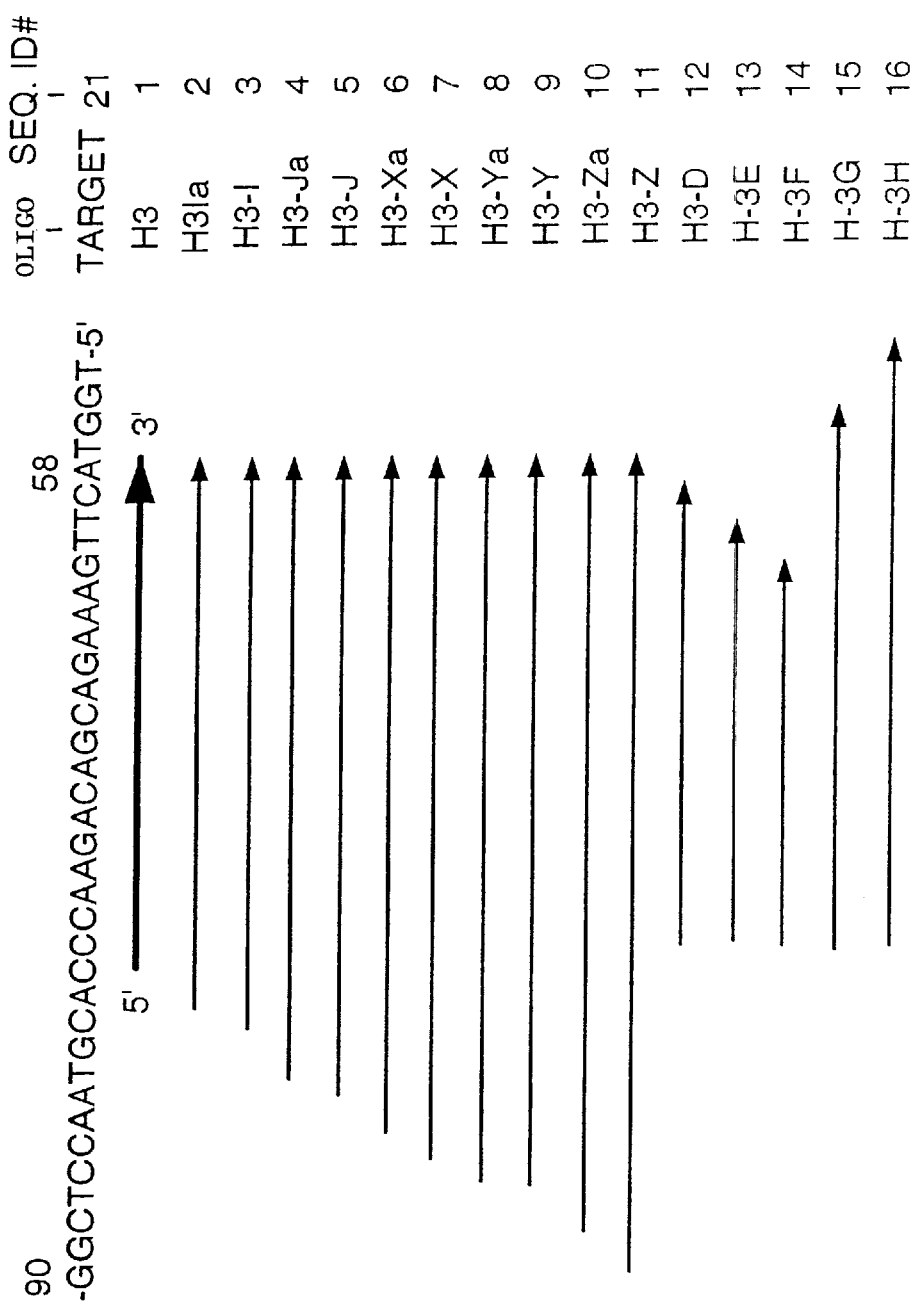
FIG. 1 is a schematic representation of the regions of the VEGF cDNA sequence that are targeted by oligonucleotides of the invention.

The patent and scientific literature referred to herein establishes the knowledge that is available to those with skill in the art. The issued U.S. patents, allowed applications, and references cited herein are hereby incorporated by reference.

The present invention provides synthetic antisense oligonucleotides specific for VEGF nucleic acid which are useful in treating diseases and disorders associated with angiogenesis and neovascularization, including retinal neovascularization, psoriasis, and the bullous diseases.

Antisense oligonucleotide technology provides a novel approach to the inhibition of gene expression (see generally, Agrawal (1992) *Trends in Biotech.* 10:152–158; Wagner (1994) *Nature* 372:333–335; and Stein et al. (1993) *Science* 261:1004–1012). By binding to the complementary nucleic acid sequence (the sense strand), antisense oligonucleotide are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17mer base sequence statistically occurs only once in the human genome, and thus extremely precise targeting of specific sequences is possible with such antisense oligonucleotides.

It has been determined that the VEGF coding region is comprised of eight axons (Tischer et al. (1994) *J. Biol. Chem.* 266:11947–11954). Three VEGF transcripts, 121, 165, and 189 amino acids long, have been observed, suggesting that an alternative splicing mechanism is involved (Leung et al. (1989) *Science* 246:1306–1309; Tischer et al. (1991) *J. Biol. Chem.* 266:11947–11954). More recently, a fourth VEGF transcript was discovered which has a length encoding 206 amino acids (Houck et al. (1991) *Mol. Endocrinol.* 5:1806–1814). Transcripts analogous to the 121 and 165 amino acid polypeptides have been identified in the bovine system (Leung et al. (1989) *Science* 246:1306–1309), and the transcript corresponding to the 165 amino acid transcript have also been identified in the rodent system (Conn et al. (1990) *Proc. Natl. Acad. Sci. (USA)* 87:1323–1327); Senger et al. (1990) *Cancer Res.* 50:1774–1778; Claffey et al. (1992) *J. Biol. Chem.* 267:16317–16322). Nucleic acid sequences encoding three forms of VEGF have also been reported in humans (Tischer et al. (1991) *J. Biol. Chem.* 266:11947–11954), and comparisons between the human and the murine VEGF have revealed greater than 85% interspecies conservation (Claffey et al. (1992) *J. Biol. Chem.* 267:16317–16322).

The oligonucleotides of the invention are directed to any portion of the VEGF nucleic acid sequence that effectively acts as a target for inhibiting VEGF expression. The sequence of the gene encoding VEGF has been reported in mice (Claffey et al., ibid.) and for humans (Tischer et al., ibid.). These targeted regions of the VEGF gene include any portions of the known exons. In addition, exon-intron boundaries are potentially useful targets for antisense inhibition of VEGF expression. One useful targeted region is around bases 58 to 90. The nucleotide sequences of some representative, non-limiting oligonucleotides specific for human VEGF have SEQ ID NOS:1–16.

The oligonucleotides of the invention are composed of ribonucleotides, deoxyribonucleotides, or a combination of both, with the 5' end of one nucleotide and the 3' end of another nucleotide being covalently linked. These oligonucleotides are at least 14 nucleotides in length, but are preferably 15 to 30 nucleotides long, with 16 to 29mers being the most common.

These oligonucleotides can be prepared by the art recognized methods such as phosphoramidate or H-phosphonate chemistry which can be carried out manually or by an automated synthesizer as described in Uhlmann et al. (*Chem. Rev.* (1990) 90:534–583) and Agrawal (*Trends Biotechnol.* (1992) 10:152–158).

The oligonucleotides of the invention may also be modified in a number of ways without compromising their ability to hybridize to VEGF mRNA. For example, the oligonucleotides may contain at least one or a combination of other than phosphodiester internucleotide linkages between the 5' end of one nucleotide and the 3' end of another nucleotide in which the 5' nucleotide phosphodiester linkage has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters.

For example, U.S. Pat. No. 5,149,797 describes traditional chimeric oligonucleotides having a phosphorothioate core region interposed between methylphosphonate or phosphoramidate flanking regions. U.S. patent application Ser. No. 08/516,454, filed on Aug. 9, 1995 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various oligonucleotides with modified internucleotide linkages can be prepared according to known methods (see, e.g., Goodchild (1990) *Bioconjugate Chem.* 2:165–187; Agrawal et al., (1988) *Proc. Natl. Acad. Sci. (USA)* 85:7079–7083; Uhlmann et al. (1990) *Chem. Rev.* 90:534–583; and Agrawal et al. (1992) *Trends Biotechnol.* 10:152–158.

The phosphorothioate linkages may be mixed Rp and Sp enantiomers, or they may be stereoregular or substantially stereoregular in either Rp or Sp form (see Iyer et al. (1995) *Tetrohedron Asymmetry* 6:1051–1054). Oligonucleotides with phosphorothioate linkages can be prepared using methods well known in the field such as phosphoramidite (see, e.g., Agrawal et al. (1988) *Proc. Natl. Acad Sci. (USA)* 85:7079–7083). or by H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide.

Other modifications include those which are internal or at the end(s) of the oligonucleotide molecule and include additions to the molecule of the internucleoside phosphate linkages, such as cholesterol, cholesterol, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O— lower alkyl group containing 1–6 saturated or unsaturated carbon atoms, or with an —O-aryl, or allyl group having 2–6 carbon atoms wherein such —O-alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. None of these substitutions are intended to exclude the native 2'-hydroxyl group in the case of ribose or 2'-H— in the case of deoxyribose. PCT Publication No. WO 94/02498 discloses traditional hybrid oligonucleotides having regions of 2'-O-substituted ribonucleotides flanking a DNA core region. U.S. patent application Ser. No. (47508-559), filed Aug. 9, 1995, discloses an "inverted" hybrid oligonucleotide which includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides. Nonlimiting examples of particularly useful oligonucleotides of the invention have 2'-O-alkylated ribonucleotides at their 3', 5', or 3' and 5' termini, with at least four or five contiguous nucleotides being so modified. Non-limiting examples of 2'-O-alkylated groups include 2'-O-methyl, 2'-O-ethyl, 2'-O-propyl, and 2'-O-butyls.

Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

A nonlimiting list of useful oligonucleotides of the invention are listed below in Table 1.

TABLE 1

| OLIGO | TARGETED SITE | SEQUENCE (5'→3') | SEQ ID NO: |
|---|---|---|---|
| H-3Ia1 | 81-62 | GCACCCAAGACAGCAGAAAG | 2 |
| H-3Ia2 | 81-62 | GCACCCAAGACAGCAGAAAG | 2 |
| H-3Ia3 | 81-62 | GCACCCAAGACAGCAGAAAG | 2 |
| H-3Ia4 | 81-62 | GCACCCAAGACAGCAGAAAG | 2 |
| H-3Ia5 | 81-62 | GCACCCAAGACAGCAGAAAG | 2 |
| H-3Ia6 | 81-62 | GCACCCAAGACAGCAAAG | 2 |
| H-3Ia7 | 81-62 | GCACCCAAGACAGCAGAAAG | 2 |
| H-3Ia8 | 81-62 | GCACCCAAGACAGCAGAAAG | 2 |
| H-3Ia9 | 81-62 | GCACCCAAGACAGCAGAAAG | 2 |
| H-3Ia10 | 81-62 | GCACCCAAGACAGCAGAAAG | 2 |
| H-3I1 | 82-62 | TGCACCCAAGACAGCAGAAAG | 3 |
| H-3I2 | 82-62 | TGCACCCAAGACAGCAGAAAG | 3 |
| H-3I3 | 82-62 | TGCACCCAAGACAGCAGAAAG | 3 |
| H-3I4 | 82-62 | TGCACCCAAGACAGCAGAAAG | 3 |
| H-3I5 | 82-62 | TGCACCCAAGACAGCAGAAAG | 3 |
| H-3I6 | 82-62 | TGCACCCAAGACAGCAGAAAG | 3 |
| H-3I7 | 82-62 | TGCACCCAAGACAGCAGAAAG | 3 |
| H-3I8 | 82-62 | TGCACCCAAGACAGCAGAAAG | 3 |
| H-3I9 | 82-62 | TGCACCCAAGACAGCAGAAAG | 3 |
| H-3I10 | 82-62 | TGCACCCAAGACAGCAGAAAG | 3 |
| H-3Ja1 | 83-62 | ATGCACCCAAGACAGCAGAAAG | 4 |
| H-3Ja2 | 83-62 | ATGCACCCAAGACAGCAGAAAG | 4 |
| H-3Ja3 | 83-62 | ATGCACCCAAGACAGCAGAAAG | 4 |
| H-3Ja4 | 83-62 | ATGCACCCAAGACAGCAGAAAG | 4 |
| H-3Ja5 | 83-62 | ATGCACCCAAGACAGCAGAAAG | 4 |
| H-3Ja6 | 83-62 | ATGCACCCAAGACAGCAGAAAG | 4 |
| H-3Ja7 | 83-62 | ATGCACCCAAGACAGCAGAAAG | 4 |
| H-3Ja8 | 83-62 | ATGCACCCAAGACAGCAGAAAG | 4 |
| H-3Ja9 | 83-62 | ATGCACCCAAGACAGCAGAAAG | 4 |
| H-3Ja10 | 83-62 | ATGCACCCAAGACAGCAGAAAG | 4 |
| H-3J1 | 84-62 | AATGCACCCAAGACAGCAGAAAG | 5 |
| H-3J2 | 84-62 | AATGCACCCAAGACAGCAGAAAG | 5 |
| H-3J3 | 84-62 | AATGCACCCAAGACAGCAGAAAG | 5 |
| H-3J4 | 84-62 | AATGCACCCAAGACAGCAGAAAG | 5 |
| H-3J5 | 84-62 | AATGCACCCAAGACAGCAGAAAG | 5 |
| H-3J6 | 84-62 | AATGCACCCAAGACAGCAGAAAG | 5 |
| H-3J7 | 84-62 | AATGCACCCAAGACAGCAGAAAG | 5 |
| H-3J8 | 84-62 | AATGCACCCAAGACAGCAGAAAG | 5 |
| H-3J9 | 84-62 | AATGCACCCAAGACAGCAGAAAG | 5 |
| H-3J10 | 84-62 | AATGCACCCAAGACAGCAGAAAG | 5 |
| H-3Xa1 | 85-62 | CAATGCACCCAAGACAGCAGAAAG | 6 |
| H-3Xa2 | 85-62 | CAATGCACCCAAGACAGCAGAAAG | 6 |
| H-3Xa3 | 85-62 | CAATGCACCCAAGACAGCAGAAAG | 6 |
| H-3Xa4 | 85-62 | CAATGCACCCAAGACAGCAGAAAG | 6 |
| H-3Xa5 | 85-62 | CAATGCACCCAAGACAGCAGAAAG | 6 |
| H-3Xa6 | 85-62 | CAATGCACCCAAGACAGCAAAG | 6 |
| H-3Xa7 | 85-62 | CAATGCACCCAAGACAGCAGAAAG | 6 |
| H-3Xa8 | 85-62 | CAATGCACCCAAGACAGCAGAAAG | 6 |
| H-3Xa9 | 85-62 | CAATGCACCCAAGACAGCAGAAAG | 6 |
| H-3Xa10 | 85-62 | CAATGCACCCAAGACAGCAGAAAG | 6 |
| H-3X1 | 86-62 | CCAATGCACCCAAGACAGCAGAAAG | 7 |

TABLE 1-continued

| OLIGO | TARGETED SITE | SEQUENCE (5'→3') | SEQ ID NO: |
|---|---|---|---|
| H-3X2 | 86-62 | CCAATGCACCCAAGACAGCAGAAAG | 7 |
| H-3X3 | 86-62 | CCAATGCACCCAAGACAGCAGAAAG | 7 |
| H-3X4 | 86-62 | CCAATGCACCCAAGACAGCAGAAAG | 7 |
| H-3X5 | 86-62 | CCAATGCACCCAAGACAGCAGAAAG | 7 |
| H-3X6 | 86-62 | CCAATGCACCCAAGACAGCAGAAAG | 7 |
| H-3X7 | 86-62 | CCAATGCACCCAAGACAGCAGAAAG | 7 |
| H-3X8 | 86-62 | CCAATGCACCCAAGACAGCAGAAAG | 7 |
| H-3X9 | 86-62 | CCAATGCACCCAAGACAGCAGAAAG | 7 |
| H-3X10 | 86-62 | CCAATGCACCCAAGACAGCAGAAAG | 7 |
| H-3Ya1 | 87-62 | TCCAATGCACCCAAGACAGCAGAAAG | 8 |
| H-3Ya2 | 87-62 | TCCAATGCACCCAAGACAGCAGAAAG | 8 |
| H-3Ya3 | 87-62 | TCCAATGCACCCAAGACAGCAGAAAG | 8 |
| H-3Ya4 | 87-62 | TCCAATGCACCCAAGACAGCAGAAAG | 8 |
| H-3Ya5 | 87-62 | TCCAATGCACCCAAGACAGCAGAAAG | 8 |
| H-3Ya6 | 87-62 | TCCAATGCACCCAAGACAGCAGAAAG | 8 |
| H-3Ya7 | 87-62 | TCCAATGCACCCAAGACAGCAGAAAG | 8 |
| H-3Ya8 | 87-62 | TCCAATGCACCCAAGACAGCAGAAAG | 8 |
| H-3Ya9 | 87-62 | TCCAATGCACCCAAGACAGCAGAAAG | 8 |
| H-3Ya10 | 87-62 | TCCAATGCACCCAAGACAGCAGAAAG | 8 |
| H-Y1 | 88-62 | CTCCAATGCACCCAAGACAGCAGAAAG | 9 |
| H-Y2 | 88-62 | CTCCAATGCACCCAAGACAGCAGAAAG | 9 |
| H-Y3 | 88-62 | CTCCAATGCACCCAAGACAGCAGAAAG | 9 |
| H-Y4 | 88-62 | CTCCAATGCACCCAAGACAGCAGAAAG | 9 |
| H-Y5 | 88-62 | CTCCAATGCACCCAAGACAGCAGAAAG | 9 |
| H-Y6 | 88-62 | CTCCAATGCACCCAAGACAGCAGAAAG | 9 |
| H-Y7 | 88-62 | CTCCAATGCACCCAAGACAGCAGAAAG | 9 |
| H-Y8 | 88-62 | CTCCAATGCACCCAAGACAGCAGAAAG | 9 |
| H-Y9 | 88-62 | CTCCAATGCACCCAAGACAGCAGAAAG | 9 |
| H-Y10 | 88-62 | CTCCAATGCACCCAAGACAGCAGAAAG | 9 |
| H-Za1 | 89-62 | GCTCCAATGCACCCAAGACAGCAGAAAG | 10 |
| H-Za2 | 89-62 | GCTCCAATGCACCCAAGACAGCAGAAAG | 10 |
| H-Za3 | 89-62 | GCTCCAATGCACCCAAGACAGCAGAAAG | 10 |
| H-Za4 | 89-62 | GCTCCAATGCACCCAAGACAGCAGAAAG | 10 |
| H-Za5 | 89-62 | GCTCCAATGCACCCAAGACAGCAGAAAG | 10 |
| H-Za6 | 89-62 | GCTCCAATGCACCCAAGACAGCAGAAAG | 10 |
| H-Za7 | 89-62 | GCTCCAATGCACCCAAGACAGCAGAAAG | 10 |
| H-Za8 | 89-62 | GCTCCAATGCACCCAAGACAGCAGAAAG | 10 |
| H-Za9 | 89-62 | GCTCCAATGCACCCAAGACAGCAGAAAG | 10 |
| H-Za10 | 89-62 | GCTCCAATGCACCCAAGACAGCAGAAAG | 10 |
| H-Z1 | 90-62 | GGCTCCAATGCACCCAAGACAGCAGAAAG | 11 |
| H-Z2 | 90-62 | GGCTCCAATGCACCCAAGACAGCAGAAAG | 11 |
| H-Z3 | 90-62 | GGCTCCAATGCACCCAAGACAGCAGAAAG | 11 |
| H-Z4 | 90-62 | GGCTCCAATGCACCCAAGACAGCAGAAAG | 11 |
| H-Z5 | 90-62 | GGCTCCAATGCACCCAAGACAGCAGAAAG | 11 |
| H-Z6 | 90-62 | GGCTCCAATGCACCCAAGACAGCAGAAAG | 11 |
| H-Z7 | 90-62 | GGCTCCAATGCACCCAAGACAGCAGAAAG | 11 |
| H-Z8 | 90-62 | GGCTCCAATGCACCCAAGACAGCAGAAAG | 11 |
| H-Z9 | 90-62 | GGCTCCAATGCACCCAAGACAGCAGAAAG | 11 |
| H-Z10 | 90-62 | GGCTCCAATGCACCCAAGACAGCAGAAAG | 11 |
| H-3D1 | 80-63 | CACCCAAGACAGCAGAAA | 12 |
| H-3D2 | 80-63 | CACCCAAGACAGCAGAAA | 12 |
| H-3D3 | 80-63 | CACCCAAGACAGCAGAAA | 12 |
| H-3D4 | 80-63 | CACCCAAGACAGCAGAAA | 12 |
| H-3D5 | 80-63 | CACCCAAGACAGCAGAAA | 12 |
| H-3D6 | 80-63 | CACCCAAGACAGCAGAAA | 12 |
| H-3D7 | 80-63 | CACCCAAGACAGCAGAAA | 12 |
| H-3D8 | 80-63 | CACCCAAGACAGCAGAAA | 12 |
| H-3D9 | 80-63 | CACCCAAGACAGCAGAAA | 12 |
| H-3D10 | 80-63 | CACCCAAGACAGCAGAAA | 12 |
| H-3E1 | 80-64 | CACCCAAGACAGCAGAA | 13 |
| H-3E2 | 80-64 | CACCCAAGACAGCAGAA | 13 |
| H-3E3 | 80-64 | CACCCAAGACAGCAGAA | 13 |
| H-3E4 | 80-64 | CACCCAAGACAGCAGAA | 13 |
| H-3E5 | 80-64 | CACCCAAGACAGCAGAA | 13 |
| H-3E6 | 80-64 | CACCCAAGACAGCAGAA | 13 |
| H-3E7 | 80-64 | CACCCAAGACAGCAGAA | 13 |
| H-3E8 | 80-64 | CACCCAAGACAGCAGAA | 13 |
| H-3E9 | 80-64 | CACCCAAGACAGCAGAA | 13 |
| H-3E10 | 80-64 | CACCCAAGACAGCAGAA | 13 |
| H-3F1 | 80-65 | CACCCAAGACAGCAGA | 14 |
| H-3F2 | 80-65 | CACCCAAGACAGCAGA | 14 |
| H-3F3 | 80-65 | CACCCAAGACAGCAGA | 14 |
| H-3F4 | 80-65 | CACCCAAGACAGCAGA | 14 |
| H-3F5 | 80-65 | CACCCAAGACAGCAGA | 14 |
| H-3F6 | 80-65 | CACCCAAGACAGCAGA | 14 |
| H-3F7 | 80-65 | CACCCAAGACAGCAGA | 14 |

TABLE 1-continued

| OLIGO | TARGETED SITE | SEQUENCE (5'→3') | SEQ ID NO: |
|---|---|---|---|
| H-3F8 | 80-65 | CACCCAAGACAGCAGA | 14 |
| H-3F9 | 80-65 | CACCCAAGACAGCAGA | 14 |
| H-3F10 | 80-65 | CACCCAAGACAGCAGA | 14 |
| H-3G1 | 80-60 | CACCCAAGACAGCAGAAAGTT | 15 |
| H-3G2 | 80-60 | CACCCAAGACAGCAGAAAGTT | 15 |
| H-3G3 | 80-60 | CACCCAAGACAGCAGAAAGTT | 15 |
| H-3G4 | 80-60 | CACCCAAGACAGCAGAAAGTT | 15 |
| H-3G5 | 80-60 | CACCCAAGACAGCAGAAAGTT | 15 |
| H-3G6 | 80-60 | CACCCAAGACAGCAGAAAGTT | 15 |
| H-3G7 | 80-60 | CACCCAAGACAGCAGAAAGTT | 15 |
| H-3G8 | 80-60 | CACCCAAGACAGCAGAAAGTT | 15 |
| H-3G9 | 80-60 | CACCCAAGACAGCAGAAAGTT | 15 |
| H-3G10 | 80-60 | CACCCAAGACAGCAGAAAGTT | 15 |
| H-3H1 | 80-58 | CACCCAAGACAGCAGAAAGTTCAT | 16 |
| H-3H2 | 80-58 | CACCCAAGACAGCAGAAAGTTCAT | 16 |
| H-3H3 | 80-58 | CACCCAAGACAGCAGAAAGTTCAT | 16 |
| H-3H4 | 80-58 | CACCCAAGACAGCAGAAAGTTCAT | 16 |
| H-3H5 | 80-58 | CACCCAAGACAGCAGAAAGTTCAT | 16 |
| H-3H6 | 80-58 | CACCCAAGACAGCAGAAAGTTCAT | 16 |
| H-3H7 | 80-58 | CACCCAAGACAGCAGAAAGTTCAT | 16 |
| H-3H8 | 80-58 | CACCCAAGACAGCAGAAAGTTCAT | 16 |
| H-3H9 | 80-58 | CACCCAAGACAGCAGAAAGTTCAT | 16 |
| H-3H10 | 80-58 | CACCCAAGACAGCAGAAAGTTCAT | 16 |

Preferably, the nucleotides bolded in the oligonucleotides above are 2'-O-alkylated, and all of the nucleotides are linked via non-phosphodiester internucleotide linkages such as phosphorothioates.

The preparation of these modified oligonucleotides is well known in the art (reviewed in Agrawal (1992) *Trends Biotechnol.* 10:152–158; Agrawal et al. (1995) *Curr. Opin. Biotechnol.* 6:12–19). For example, nucleotides can be covalently linked using art-recognized techniques such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron Lett.* 28: (31) :3539–3542); Caruthers et al. (1987) *Meth. Enzymol.* 154:287–313; U.S. Pat. No. 5,149,798). Oligomeric phosphorothioate analogs can be prepared using methods well known in the field such as methoxyphosphoramidite (see, e.g., Agrawal et al. (1988) *Proc. Natl. Acad. Sci.* (*USA*) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

The synthetic antisense oligonucleotides of the invention in the form of a therapeutic formulation are useful in treating diseases, and disorders, and conditions associated with angiogenesis and neovascularization including, but not limited to, retinal neovascularization, tumor growth, wound healing, bullous pemphigoid, dermatitis herpetiformis, erythema multiforme, and psoriasis. In such methods, a therapeutic amount of a synthetic oligonucleotide of the invention and effective in inhibiting the expression of vascular endothelial growth factor is administered to a cell. This cell may be part of a cell culture, a neovascularized tissue culture, or may be part or the whole body of an animal such as a human or other mammal. Administration may be topical, intralesional, bolus, intermittent, or continuous, depending on the condition and response, as determined by those with skill in the art. In some preferred embodiments of the methods of the invention described above, the oligonucleotide is administered locally (e.g., intraocularly or interlesionally) and/or systemically. The term "local administration" refers to delivery to a defined area or region of the body, while the term "systemic administration is meant to encompass delivery to the whole organism by oral ingestion, or by intramuscular, intravenous, subcutaneous, or intraperitoneal injection.

Such methods can be used to treat retinopathy of prematurity (ROP), diabetic retinopathy, age-related macular degeneration, sickle cell retinopathy, neovascular glaucoma, retinal vein occlusion, and other hypoxic diseases.

The synthetic oligonucleotides of the invention may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of VEGF expression or which will reduce neovascularization. For example, combinations of synthetic oligonucleotides, each of which is directed to different regions of the VEGF mRNA, may be used in the pharmaceutical compositions of the invention. The pharmaceutical composition of the invention may further contain nucleotide analogs such as azidothymidine, dideoxycytidine, dideosyinosine, and the like. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-VEGF or anti-neovascularization factor and/or agent to minimize side effects of the anti-VBGF factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include compounds such as cyclodextrins and the like which enhance delivery of oligonucleotides into cells, as described by Zhao et al. (in press), or slow release polymers.

As used herein, the term "therapeutically effective amount" means the total amount of each active component of the pharmaceutical composition or method that is sufficient to show a meaningful patient benefit, i.e., healing of chronic conditions characterized by neovascularization or a reduction in neovascularization, itself, or in an increase in rate of healing of such conditions, or in a reduction in aberrant epidermal lesions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one, two, or more of the synthetic oligonucleotides of the invention is administered to a subject afflicted with a disease or disorder related to neovascularization, or to a tissue which has been neovascularized. The synthetic oligonucleotide of the invention may be administered in accordance with the method of the invention either alone of in combination with other known therapies for neovascularization, angiogenesis, or dermatoses related thereto. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

Administration of the synthetic oligonucleotide of the invention used in the pharmaceutical composition or to practice the method of the present invention can be carried out in a variety of conventional ways, such as topical or intralesional administration, intraocular, oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, subcutaneous, intramuscular, intraocular, or intraperitoneal injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, intraperitoneal, or intraocular injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

When administered topically or intralesionally as a liquid, doses ranging from 0.01% to 10% (weight/volume) may be used. When administered in liquid form, a liquid carrier such as water, petroleum, oils of animal or plant origin such as peanut oil, mineral oil, soybean oil, sesame oil, or synthetic oils may be added. Topical administration may be by liposome or transdermal time-release patch.

The amount of synthetic oligonucleotide in the pharmaceutical composition of the present invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 10 µg to about 20 mg of synthetic oligonucleotide per kg body or organ weight.

The duration of intravenous therapy using the pharmaceutical composition of the present invention will vary, depending on the severity of the disease being treated and the condition and potential idiosyncratic response of each individual patient. Ultimately the attending physician will decide on the appropriate duration of intravenous therapy using the pharmaceutical composition of the present invention.

Some diseases lend themselves to acute treatment while others require to longer term therapy. Proliferative retinopathy can reach a threshold in a matter of days as seen. in ROP, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also smolder in the proliferative phase for considerably longer. Diabetic retinopathy will eventually become quiescent as the vasoproliferative signal diminishes with neovascularization or destruction of the retina.

Both acute and long term intervention in retinal disease are worthy goals. Intravitreal injections of oligonucleotides against VEGF can be an effective means of inhibiting retinal neovascularization in an acute situation. However for long term therapy over a period of years, systemic delivery (intraperitoneal, intramuscular, subcutaneous, intravenous)

either with carriers such as saline, slow release polymers, or liposomes should be considered.

In some cases of chronic neovascular disease, systemic administration of oligonucleotides may be preferable. Since the disease process concerns vessels which are abnormal and leaky, the problem of passage through the blood brain barrier may not be a problem. Therefore, systemic delivery may prove efficacious. The frequency of injections is from continuous infusion to once a month, depending on the disease process and the biological half life of the oligonucleotides.

In addition to inhibiting neovascularization in vivo, antisense oligonucleotides specific for VEGF are useful in determining the role of this cytokine in processes where neovascularization is involved. For example, this technology is useful in in vitro systems which mimic blood vessel formation and permeability, and in in vivo system models of neovascularization, such as the murine model described below.

A murine model of oxygen-induced retinal neovascularization has been established which occurs in 100% of treated animals and is quantifiable (Smith et al. (1994) *Invest. Ophthamol. Vis. Sci.* 35:101–111). Using this model, a correlation has been determined between increasing expression of VEGF message and the onset of retinal neovascularization in the inner nuclear and ganglion cell layers (i.e., in Müller cells) (Pierce et al. (1995) *Proc. Natl. Acad. Sci. (USA)* (in press). This result has been confirmed by Northern blot and in situ hybridization analysis of whole retinas at different time points during the development of neovascularization (Pierce et al., ibid.).

Oligonucleotides of the invention are also useful in a method of reducing the expression of VEGF. The target VEGF expression can be in vitro or in any cell which expresses VEGF. In this method, nucleic acid specific for VEGF is contacted with an oligonucleotide of the invention such that transcription of the nucleic acid to mRNA and/or protein is reduced or inhibited.

Figure 2:
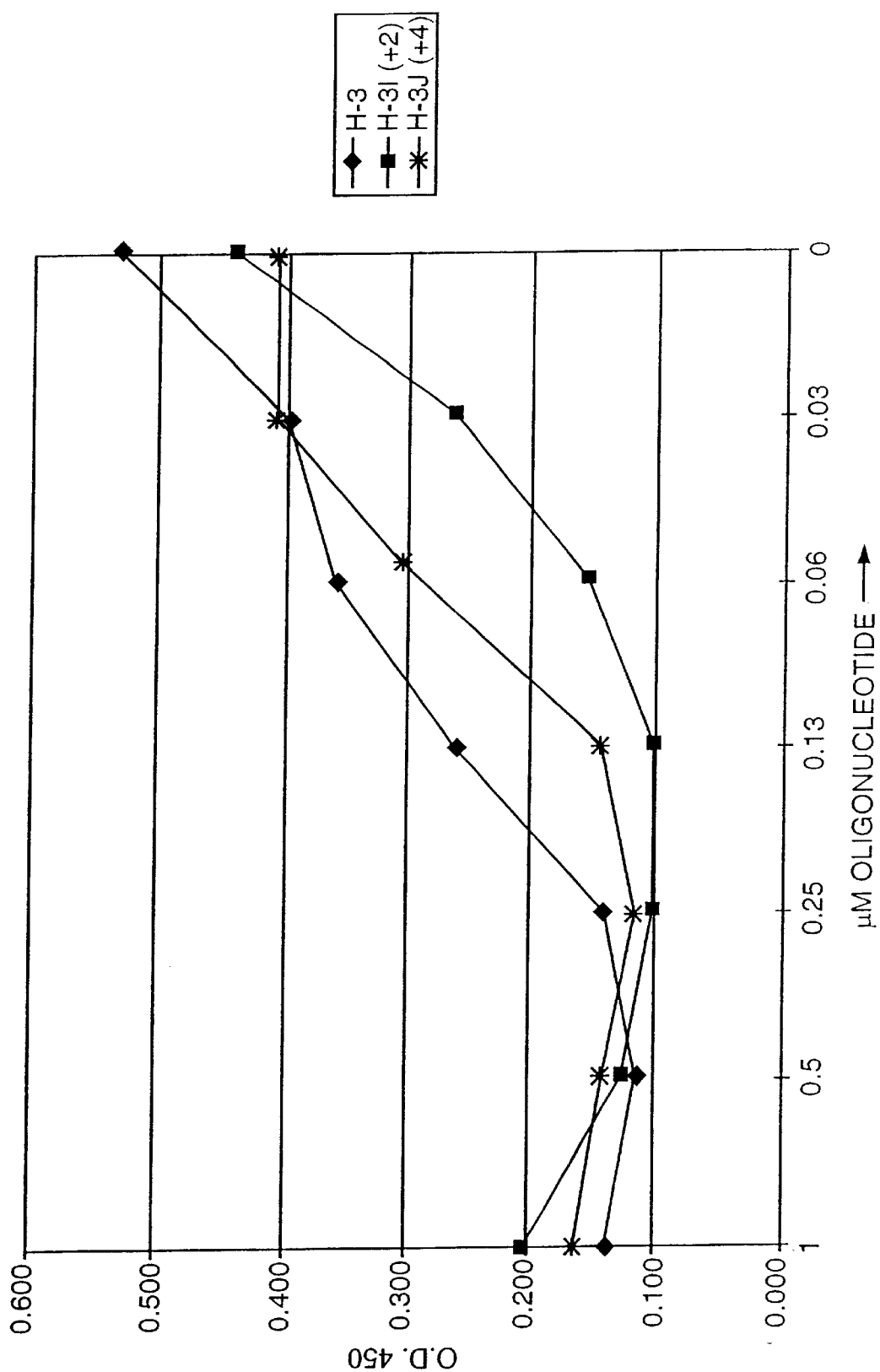
FIG. 2 is a graphic representation of ELISA results demonstrating the ability of oligonucleotides H3-I and H3-J to inhibit VEGF expression induced by cobalt chloride ($CoCl_2$)
Figure 3:
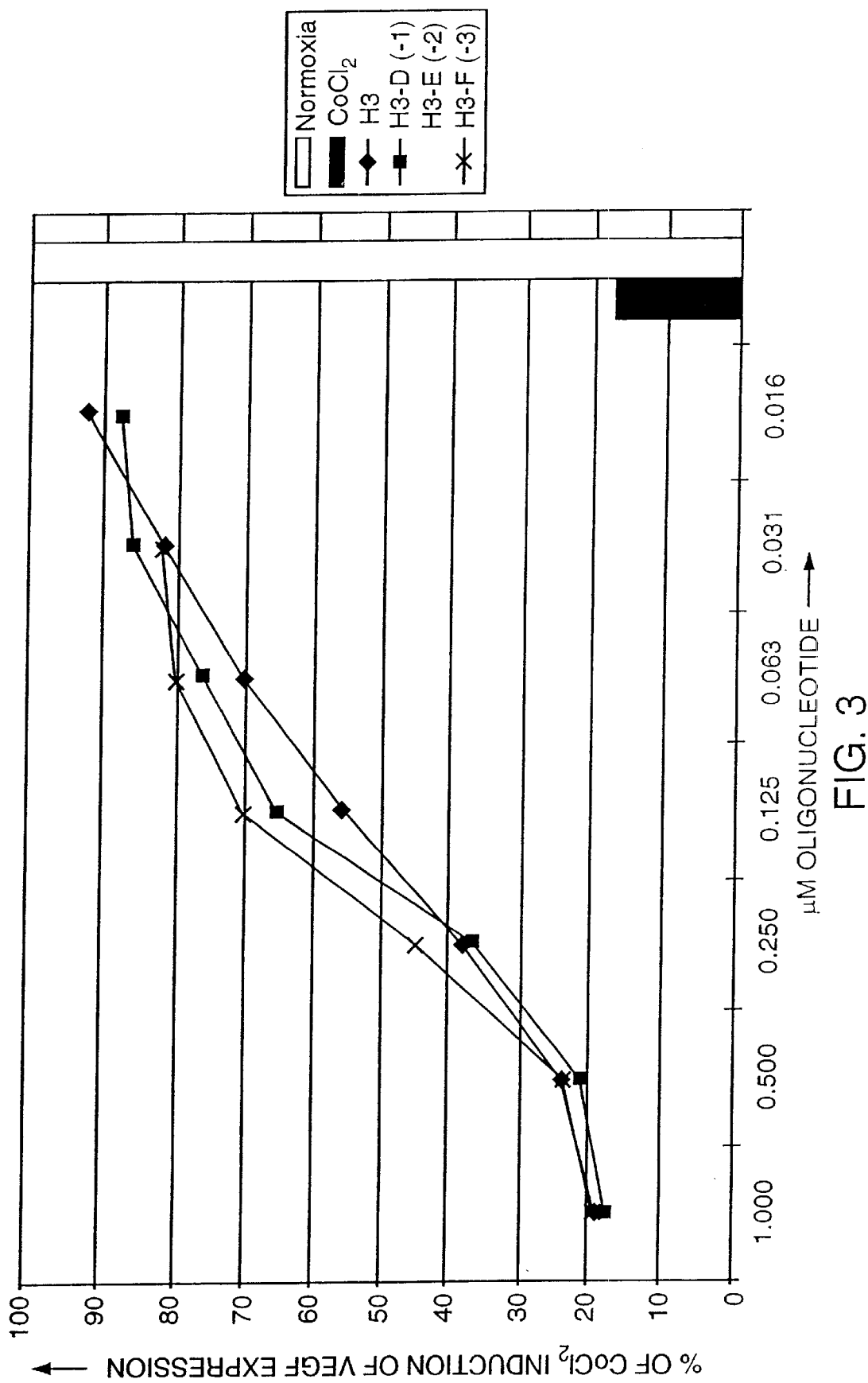
FIG. 3 is a graphic representation of ELISA results demonstrating the ability of oligonucleotides H3-D H3-E, H3-F to inhibit VEGF expression induced by cobalt chloride.
Figure 4:
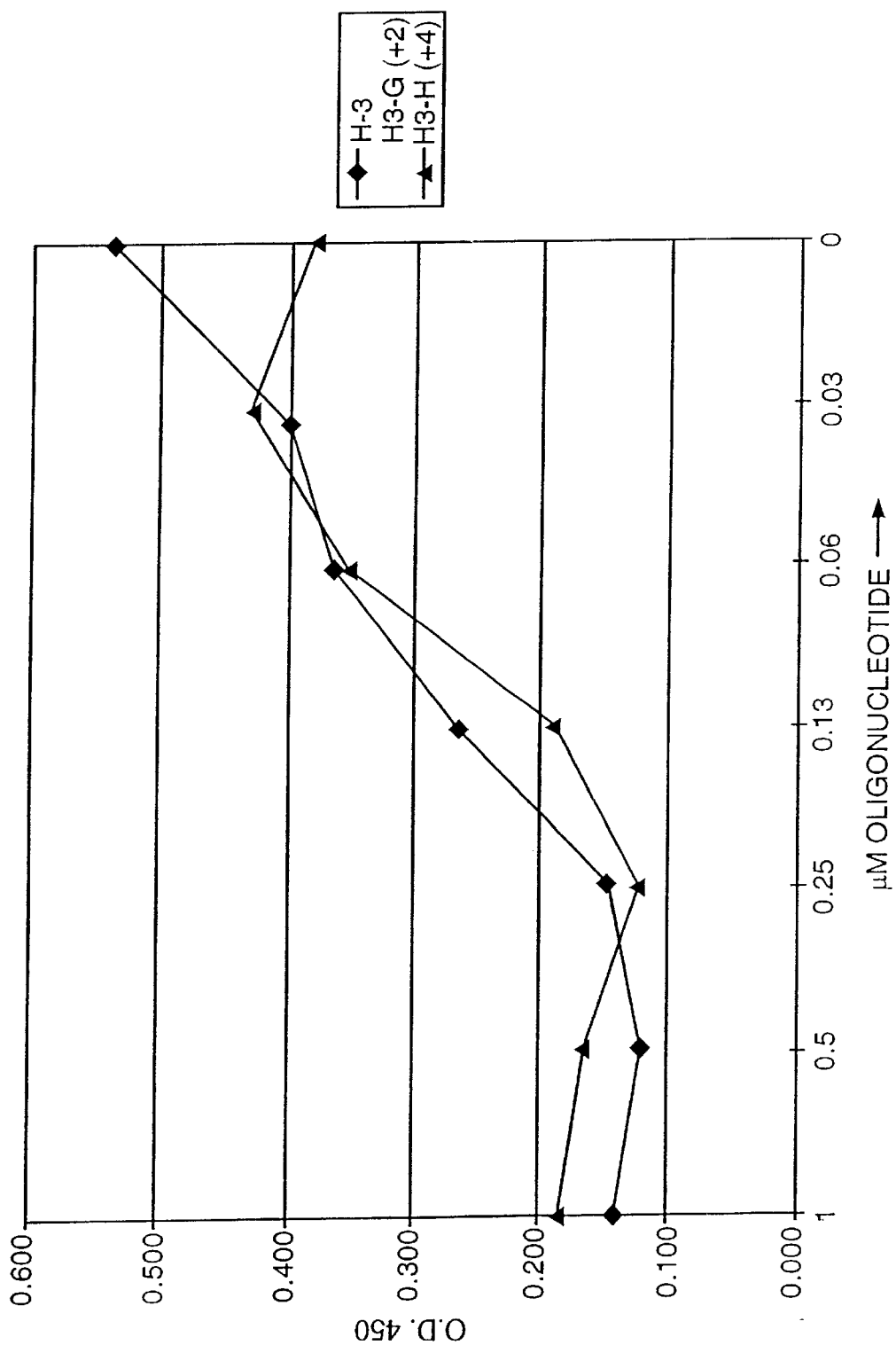
FIG. 4 is a graphic representation of ELISA results demonstrating the ability of oligonucleotides H3-G and H3-H to inhibit VEGF expression induced by cobalt chloride.
Figure 5:
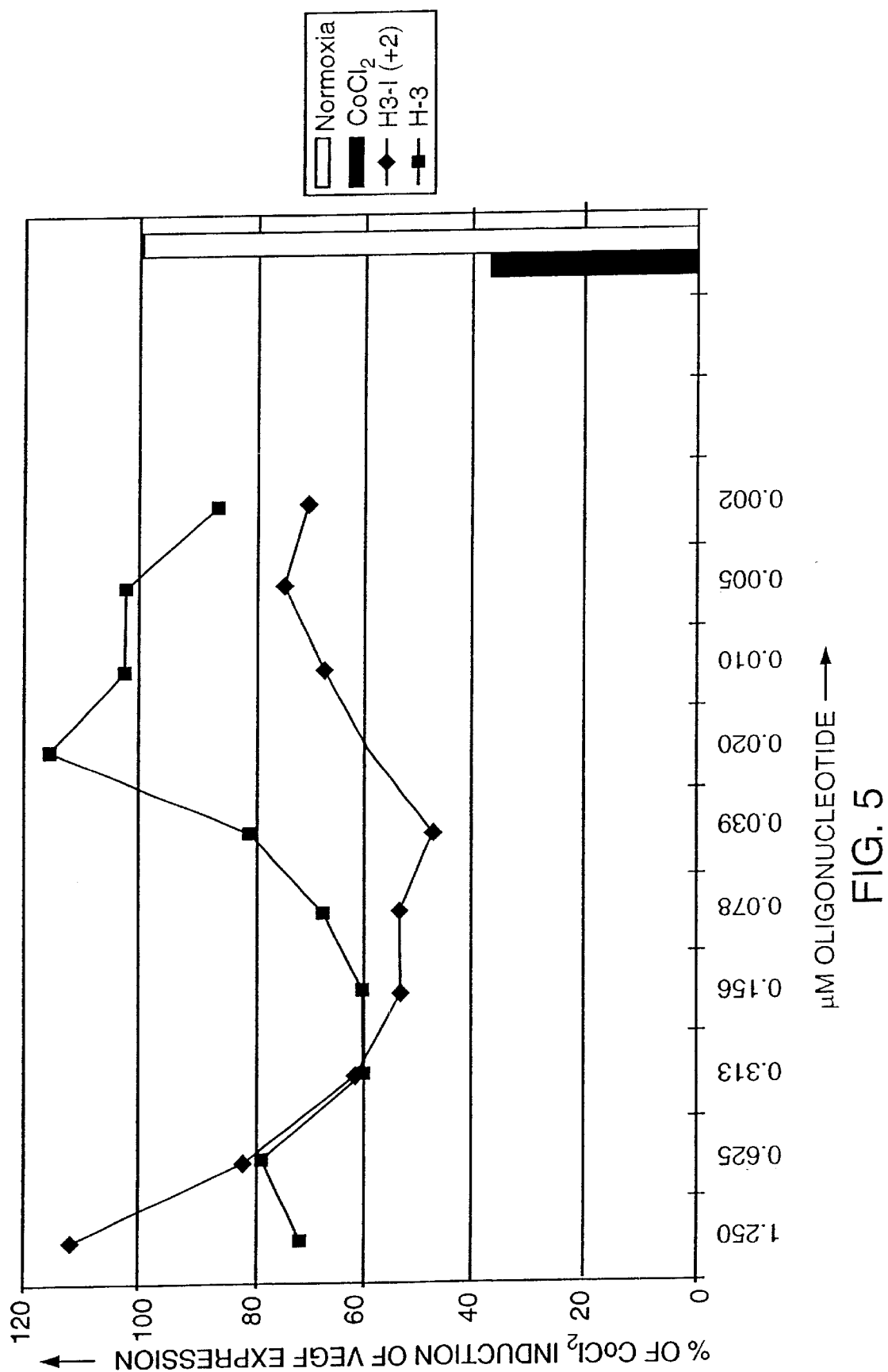
FIG. 5 is a graphic representation of ELISA results demonstrating the ability of oligonucleotides H3 and H3-I to inhibit VEGF expression induced by cobalt chloride in M21 human melanoma cells in vitro.
Figure 6:
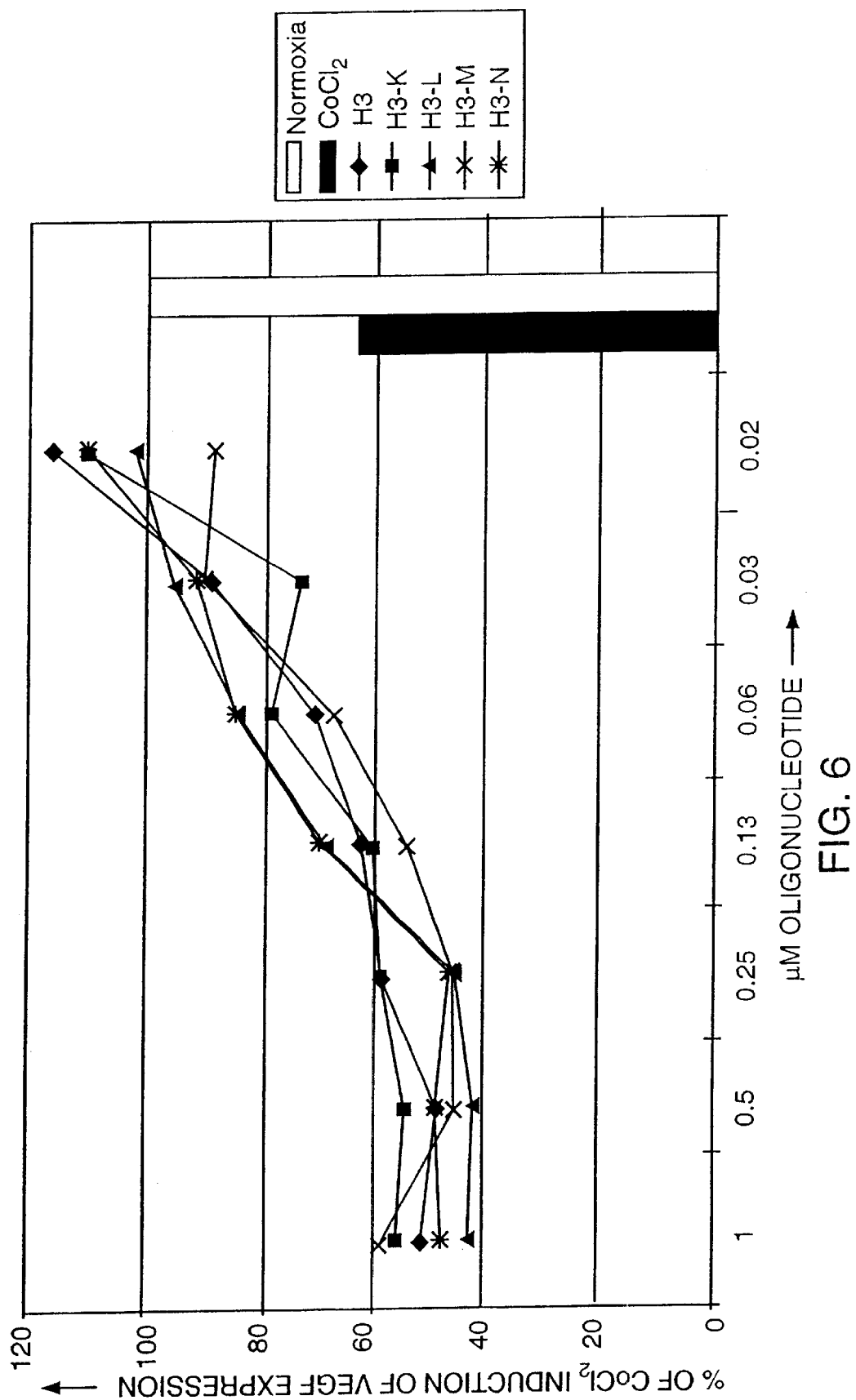
FIG. 6 is a graphic representation of ELISA results demonstrating the ability of modified H3 oligonucleotides to inhibit VEGF expression induced by cobalt chloride (H3-K: all 2'-O-methylated phosphorothioate ribonucleotides; H3-L: five 5' 2'-O-alkylated phosphorothioate ribonucleotides, the remainder, phosphorothioate deoxyribonucleotides; H3-M: five 3' 2'-O-alkylated phosphorothioate ribonucleotides; the remainder, phosphorothioate deoxyribonucleotides; and R3-N: five 3' 2'-O-alkylated phosphorothioate ribonucleotides, five 5' 2'-O-alkylated phosphorothioate ribonucleotides, and the remainder, phosphorothioate deoxyribonucleotides)

That oligonucleotides of the invention can inhibit VEGF expression at the protein level can be demonstrated using an ELISA which specifically detects human VEGF and a VEGF-expressing cell line such as a human glioblastoma (e.g., U373 ATCC Ac. no. HTB17, American Type Culture Collection, Rockville, Md.) or a human melanoma (e.g., SK-MEL-2, ATCC Ac. no. HTB68, American Type Culture Collection, Rockville, Md.; or M21). Briefly, when a human glioblastoma cell line U373 and a human melanoma cell line E21 were treated with VEGF-specific oligonucleotides of the invention, these cells stop expressing VEGF in a sequence-specific manner, as shown in FIGS. 2, 3, and 4, and in FIG. 5, respectively. FIG. 6 demonstrates that modification of the oligonucleotides does not reduce their inhibitory activity. Oligonucleotides of the invention also reduced VEGF mRNA expression, as demonstrated by the Northern analyses described in EXAMPLE 4 below.

VEGF's role in tumor formation in vivo can be demonstrated using an athymic mouse injected with as an animal model. M21 cells are known to generate palpable tumors in mice in about 1 to 1.5 weeks. Alternately, a U373 cell line which has been passed through an athymic mouse in the presence of Engelbreth Holm Swarm (EMS) tumor matrix (Matrigel™, Collaborative Research, Waltham, Mass.) may be used. When mice are injected with VEGF-specific oligonucleotides of the invention, there will be a reduction in tumor weight and volume if VEGF expression is reduced by oligonucleotides or pharmaceutical formulations of the invention.

That VEGF plays a role in retinal neovascularization has been shown using the murine model of neovascularization described above. Three independent experiments were performed using antisense oligonucleotides specific for VEGF (JG-3 (SEQ ID NO:17), JG-4, (SEQ ID NO:18), and Vm (SEQ ID NO:19), and a corresponding sense oligonucleotide (V2 (SEQ ID NO:20). These oligonucleotides were designed using the known nucleic sequence of murine VEGF (Claffee et al. (1992) *J. Biol. Chem.* 267:16317–16322). The sequence of the Vm oligonucleotide is targeted to the sequence surrounding the translational TGA stop site (TGA). The sequence of JG-4 is targeted to the sequence 5' to and containing the ATG of the translational start site of the murine VEGF molecule. The sequence of JG-3 is targeted to the 5' untranslated region, and the V2 sense sequence is targeted to the sequence surrounding the translational start site (ATG).

Figure 7:
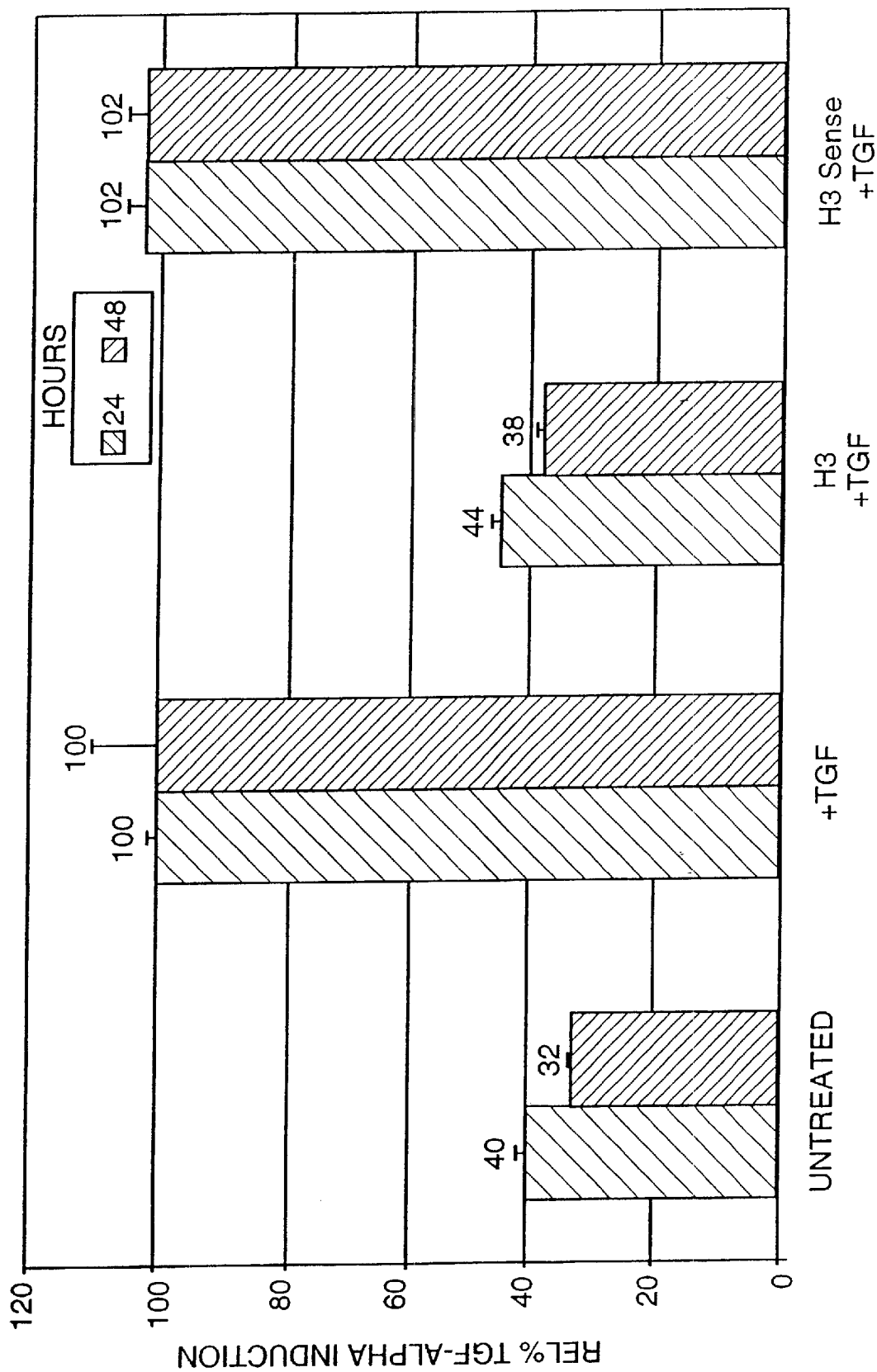
FIG. 7 is a graphic representation of the results of an ELISA in which the expression of TGF-induced VEGF in human keratinocytes in the presence and absence of oligonucleotides of the invention is shown.

That oligonucleotides of the invention can down regulate the expression VEGF in human epidermal keratinocytes, and hence, have a clinical application in the treatment of psoriasis and the bullous diseases, were demonstrated in culture system that mimics the in vivo psoriasic conditions of human skin cells. This system was developed with the knowledge that TGFα, known to be overexpressed in the epidermis of psoriasic skin lesions, induces VEGF expression at the RNA and protein level in cultured human keratinocytes (Detmar et al. (1995) *J. Invest. Dermatol.* 105:44–50). Thus, in the test system, normal human epidermal keratinocytes were cultured in the presence of TGFα. Oligodeoxynucleotides of the invention used in this study were targeted to a region adjacent to the translational start site which is conserved in all VEGF family members. These oligonucleotides can be taken up by post-confluent NAEK's as determined by flow cytometric studies which showed an increase in fluorescence of cells treated with fluorescein-labelled oligonucleotides. These oligonucleotides, which inhibit $CoCl_2$ and hypoxia induced VBGF/VPF expression at the levels of mRNA and protein, were also found to inhibit the TGFα-dependent induction of VEGF expression in normal human epidermal keratinocytes (FIG. 7).

Figure 8:
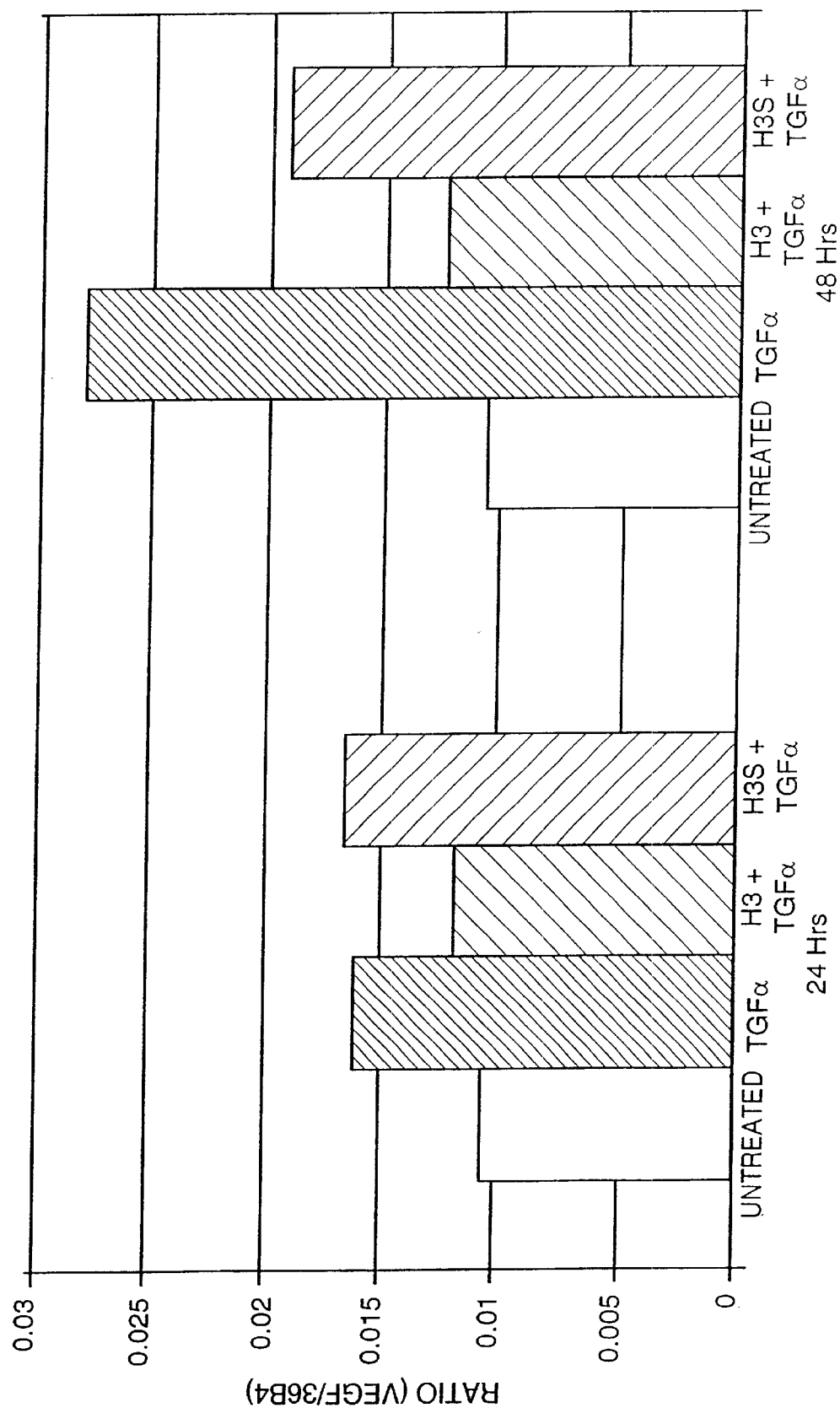
FIG. 8 is a graphic representation of the results of a Northern blot analysis showing the ability of PS oligonucleotides of the invention to inhibit expression of VEGF mRNA in NHEK cells 24 and 48 hours after oligonucleotide treatment.

In order to see if a decrease in VEGF/VPF protein was paralleled by a decrease in VEGF mRNA, confluent keratinocytes were treated with or without phosphorothioate oligonucleotides and lipofectin for eight hours followed by replacement of the medium with basal medium containing elevated levels of TGFα or the medium, alone. Supernatants were collected at 24 and 48 hours and analyzed by Northern blot for RNA and by ELISA for protein expression. Total RNA was extracted from the cells as described in the exemplification, below, and analyzed by Northern blot. The results in FIG. 8 show an increase of VEGF RNA at 24 and 48 hours in cells treated with TGFα in the presence or absence of sense or mismatched phosphorothioate oligonucleotides. Cells treated with the antisense oligonucleotide phosphorothioates showed a reduced level of VEGF RNA to near basal levels for both time points examined. This decrease in VEGF RNA levels by antisense oligonucleotide phosphorothioate treatment was paralleled by a decrease in VEGF protein accumulation in the media as assayed by capture ELISA. Analysis of the cell culture media for control and mismatch oligonucleotide phosphorothioate-treated cells showed little or no effect on the production of VEGF protein levels.

Figure 9:
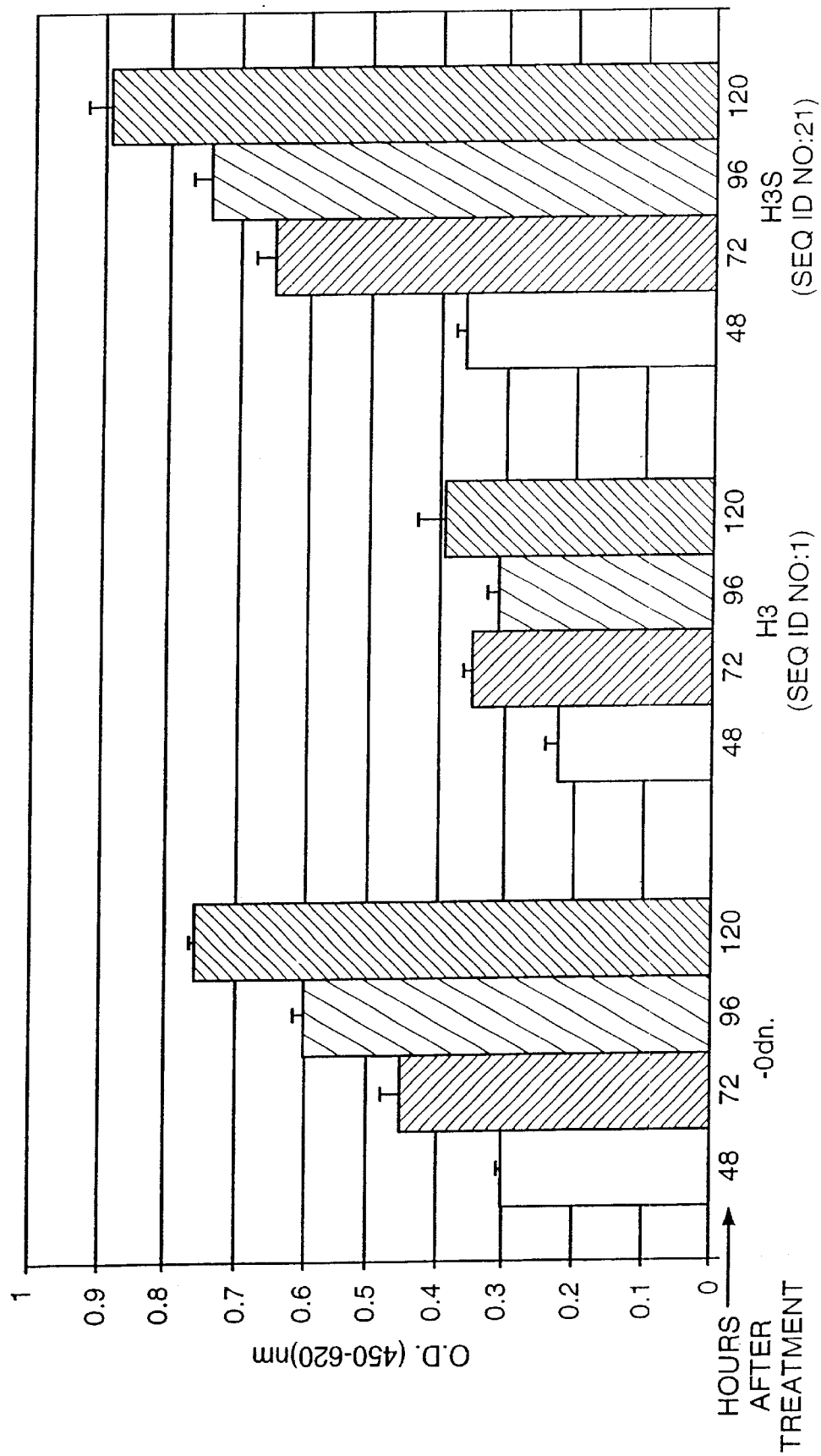
FIG. 9 is a graphic representation of the results of a capture ELISA showing the ability of PS oligonucleotides of the invention to inhibit expression of VEGF protein in NHEK cells 24, 48, 72, 96, and 120 hours after oligonucleotide treatment.

To determine how long inhibition of VEGF protein expression is maintained after treatment with antisense oligonucleotides of the invention, cells were treated with oligonucleotide phosphorothioates and lipofectin for eight hours. Then medium containing TGF4 was added. Supernatants were collected at 48, 72, 96, and 120 hours post-oligonucleotide phosphorothioate treatment and TGFα addition, and assayed by capture ELISA for VEGF protein. The results shown in FIG. 9 demonstrate that inhibition of VEGF protein expression is maintained for 48 hours and continues out to 120 hours. The control sense oligonucleotide phosphorothioate, H3S (SEQ ID NO:21), showed only a slight stimulatory effect. All keratinocytes appeared viable by light microscopy.

The following examples illustrate the preferred modes of making and practicing the present invention, but are not meant to limit the scope of the invention since alternative methods may be utilized to obtain similar results.

EXAMPLE 1

Preparation of VEGF-Specific Oligonucleotides

Human VEGF cDNA is transcribed in vitro using an in vitro eucaryotic transcription kit (Stratagene, La Jolla, Calif.). The RNA is labelled with $^{32}$P using T-4 polynucleotide kinase as described by (Sambrook et al. (1989) *Molecular Cloning; a Laboratory Manual*, Cold Spring Harbor Laboratory Press, NY, Vol. 1, pp. 5.71). The labelled RNA is incubated in the presence of a randomer 20mer library and RNase H, an enzyme which cleaves RNA-DNA duplexes (Boehringer Mannheim, Indianapolis, Ind.). Cleavage patterns are analyzed on a 6% polyacrylamide urea gel. The specific location of the cleaved fragments is determined using a human VEGF sequence ladder (Sequenase Kit, United States Biochemical, Cleveland, Ohio).

Oligonucleotides having sequences complementary to VEGF nucleic acid determined as described above were synthesized on a Pharmacia Gene Assembler series synthesizer using the phosphoramidite procedure (see, e.g., Uhlmann et al. (*Chem. Rev.* (1990) 90:534–583; Agrawal (1992) *Trends in Biotech*. 10:152–158; Agrawal et al. (1995) *Curr. Opin. Biotechnol*. 6:12–19). Following assembly and deprotection, oligonucleotides were ethanol precipitated twice, dried, and suspended in phosphate-buffered saline (PBS) at the desired concentration.

The purity of these oligonucleotides was tested by capillary gel electrophoreses and ion exchange HPLC. Endotoxin levels in the oligonucleotide preparation was determined using the Luminous Amebocyte Assay (Bang (1953) *Biol. Bull*. (Woods Hole, Mass.) 105:361–362).

EXAMPLE 2

Human Cell Culture

U373 human glioblastoma cells (American Type Culture Collection, Rockville, Md., ATCC Ac. no. HTB17) were cultured in Dulbecco's modified Earls (DME) medium containing glucose (4500 mg/ml) and 2 mM glutamate (Mediatech, Washington, D.C.) supplemented with penicillin/streptomycin (100 IU/MI/100 mcg/ml, Mediatech, Washington, D.C.). The cells were cultured at 37° C. under 10% $CO_2$. The cells were plated in 96 well tissue culture dishes (Costar Corp., Cambridge, Mass.) and maintained as above. The cells were placed under anoxic conditions for 18–20 hours using an anaerobic chamber (BBL Gas Pak, Cockeysville, Md.) or in the presence of 250 $\mu$M $CoCl^2$.

Normal human epidermal keratinocytes (Clonetics, San Diego, Calif.) were grown as recommended in Keratinocyte Growth Medium, KGM (Clonetics, San Diego, Calif.) or Keratinocyte Basal Medium, KBM (Clonetics, San Diego, Calif.). Cells for all experiments were used at passage 2 or 3 in 10% $CO_2$. For antisense experiments, cells were treated post confluence in P 100's or 24 well plates (Costar®, Cambridge, Mass.) with Lipofectin™ (Gibco BRL, Gaithersburg, Md.) and phosphorothioate oligodeoxynucleotides in KBM for 6–8 hours at which time the media was replaced with KBM with or without TGFα (Gibco BRL, Gaithersburg, Md.) at 100 ng/ml. The medium and cells were collected at 24 or 48 hours post-TGFα induction and used for ELISA and RNA analysis.

EXAMPLE 3

ELISA VEGF Protein Study

U373 glioblastoma cells were plated in a 96 well tissue culture dish and treated overnight with varying concentrations of antisense oligonucleotides against human VEGF in the presence of 5 $\mu$g/ml lipofectin. The cells were refed after 7 to 12 hours with fresh media and allowed to recover for 5 to 7 hours. The dishes were placed under hypoxic conditions for 18 to 20 hours using an anaerobic chamber (Gas Pac, Cockeysville, Md.) or in the presence of 250 $\mu$M $CoCl_2$. Cells maintained under normoxic conditions served as uninduced controls. The media was analyzed using the antigen capture ELISA assay described below (approximately 24 hours post treatment).

The culture medium from the cells described in EXAMPLE 2 was analyzed for VEGF protein as follows. 96-well plates (Maxizorb ELISA Nunc A/S, Camstrup, Denmark) were treated overnight at 4° C. with 100 $\mu$l/well of the capture antibody, a monoclonal antibody against human VEGF (R&D Systems, Minneapolis, Minn., 2.5 $\mu$g/ml in 1×PBS). The wells were washed three times with 1×PBS/0.05% Tween-20 (United States Biochemical, Cleveland, Ohio) using a plate washer (Dynatech, Gurnsey Channel Islands). Non-specific binding sites in the wells were blocked by adding 2% normal human serum (200 $\mu$l) and incubating the plate at 37° C. for 2 hours. This blocking solution was removed and 200 $\mu$l conditioned medium containing human VEGF added to each well and incubated at 37° C. for 2 to 3 hours or overnight at 4° C. The plates were washed as described above. 100 $\mu$l of the primary antibody (618/619, 2 $\mu$g/ml in normal human serum) was added to each well and incubated at 37° C. for 1 to 2 hours. The primary antibody was an affinity purified rabbit anti-human VEGF polyclonal). The plates were washed as described above. 100 $\mu$l of the detection antibody, a horse radish peroxidase-labelled goat anti-rabbit IgG monoclonal antibody (1:10,000, Vector Laboratories, Burlinggame, Calif.), was added to each well and incubated at 37° C. for 1 hour. The plates were washed as described above. The wells were developed using the TMB microwell peroxidase developing system (Kirkegaard and Perry, Gaithersburg, Md.), and quantified at 450 nm using a Ceres 900 plate reader (Bio-Tek Instruments, Inc., Winooski, Vt.). The linear range of this assay is between 2 ng and 0.01 ng human VEGF. Representative results are shown in FIGS. 2–6.

EXAMPLE 4

Northern Blot Analysis

In order to determine the level at which inhibition of VEGF expression occurs in cells in the presence of an oligonucleotide of the invention, Northern blotting was carried out. Human U373 cells cultured as described in EXAMPLE 2 above were plated in 100 mm tissue culture dishes and treated for 12 hours in the presence of 5 $\mu$g/ml lipofectin (Gibco-BRL, Gaithersburg, Md.) as a lipid-carrier with oligonucleotide H-3 (SEQ ID NO:1) and sense control (SEQ ID NO:21) at 0.05 µM, 0.5 µM, and 2.0 µM, respectively. The cells were refed after 7 to 8 hours with fresh media. The cells were placed in hypoxia for 18 to 20 hours or in the presence of 250 µM $CoCl^2$, and total RNA was isolated using Trizol™ (Gibco-BRL, Gaithersburg, Md.) and the single-step acid guanidinium thiocyanate-phenol-chloroform extraction method described by Chomczynski et al. (*Anal. Biochem.* (1987) 162:156–159). Northern blotting was performed according to the methods of Sambrook et al. (*Molecular Cloning: a Laboratory Manual*, Cold Spring Harbor Laboratory Press, NY) (1989) Vol. 1, pp. 7.38) or Arcellana-Panlilio et al. (*Meth. Enz.* (1993) 225:303–328). All RNA signals were quantified on a Phosphorimager (BioRad, Hercules, Calif.) and normalized using the 36B4 cDNA probe (Laborda (1991) *Nucleic Acids Res.* 19:3998). RNA expression was reduced in the presence of VEGF-specific oligonucleotides of the invention, and is not significantly affected by the presence of control sense oligonucleotide.

Alternatively, RNA was prepared from normal human epidermal keratinocytes, as described in EXAMPLE 2, using TRIzol™ (Gibco BRL, Gaithersburg, Md.) as manufacturers directions. Ten micrograms of total RNA was electrophoresed on a 1% formaldehyde gel and transferred onto Zeta-Probe® (BioRad, Hercules, Calif.). The blot was hybridized to a randomer primed simian VEGF cDNA and a cDNA, 36B4, a ribosomal associated protein to control for loading. Washes were performed as manufacturers directions. The blot was exposed to BIOMAX™MR Film (Eastman Kodak Company, Rochester, N.Y.).

Data from the Northern blot demonstrates a disease in the amount of VEGF RNA in tells treated with the antisense molecule H3 and little or no effect with the control sense phosphorothioate oligonucleotide, H3S.

EXAMPLE 5

In vivo Studies

A. Matrigel Studies

U373 glioblastoma cells were treated with 0.5 µM antisense phosphorothioate oligodeoxynucleotide (H-3, SEQ ID NO:1) or control (H3-sense phosphorothioate oligonucleotide; SEQ ID NO:21) for 7 hours in the presence of 5 µg/µl Lipofectin (Gibco-BRL, Gaithersburg, Md.). $1 \times 10^6$ oligonucleotide-treated cells were mixed with 250 µl Matrigel™ (Collaborative Research, Waltham, Mass.; 10–12 mg/ml) and injected subcutaneously into 6–8 week old athymic mice (about 20 g) (Charles River Laboratories, Wilmington, Mass.) on both the left and right sides. These cells respond to hypoxia and express increased levels of VEGF. The mice were maintained ad libitum and sacrificed 8 days post injection. The skin was dissected to expose the Matrigel pellet. Gross photography of the surrounding blood vessels was performed with a Zeiss Macroscope. The Matrigel plugs were removed and fixed in formalin for paraffin embedding and histological analysis. Tissue sections were stained with hematoxylin and eosin for quantitation of blood vessel growth into the Matrigel plug.

The injection of Matrigel alone resulted in a clear plug with no apparent angiogenesis. Matrigel plugs combined with U373 glioblastoma cells contained visible hemhorraging. In addition, the capillary bed surrounding the plug was more dense and the blood vessels were more tortuous. Athymic mice injected with Matrigel plugs combined with antisense oligonucleotide-treated cells generated less angiogenesis than the mice injected with Matrigel plugs and either untreated cells or cells pretreated with the control oligonucleotide. Matrigel plugs containing antisense treated cells also had less visible hemhorraging. The results suggest that antisense oligonucleotide treatment inhibit VEGF-induced angiogenesis.

B. Tumor Studies 6 week old athymic mice (about 20 g) are purchased from Charles River Laboratories. Human melanoma M21 cells or human glioblastoma U373 cells which have been passaged through athymic mice in the presence of Matrigel are injected subcutaneously $(2–20+10^6)$ into the flank of athymic mice. Palpable tumors are generated in 1–2 weeks. Subcutaneous antisense or sense control oligonucleotide injections begin one day following the injection of the tumor cells. The concentration of oligonucleotide is determined and ranges between 5 and 50 mg/kg. Animals are then injected over a period of three weeks. They are then sacrificed and, the tumors removed. Tumors are analyzed initially for weight and volume. In addition, analysis includes sectioning and staining for VEGF/VPF protein using an anti-human VEGF/VPF monoclonal antibody (R&D Systems, Minneapolis, Minn.) or VEGF/VPF RNA using in situ hybridization techniques. Mice injected with antisense oligonucleotides of the invention are expected to have smaller tumors than those injected with vehicle or the control.

EXAMPLE 6

Animal Model of Retinal Neovascularization

A. Preparation of Oligonucleotides

Synthesis of the following oligonucleotides: JG-3 (SEQ ID NO:17), JG-4 (SEQ ID NO:18), Vm (SEQ ID NO:19), and V2 (SEQ ID NO:20), was performed as described in Example 1.

B. Preparation of Animal Model

Seven day postnatal mice (P7, C57b1/6J, (Children's Hospital Breeding Facilities, Boston, Mass.) were exposed to 5 days of hyperoxic conditions (75+/-2%) oxygen in a sealed incubator connected to a Bird 3-M oxygen blender (flow rate: 1.5 liters/minute; Bird, Palm Springs, Calif.). The oxygen concentration was monitored by means of an oxygen analyzer (Beckman, Model D2, Irvine, Calif.). After 5 days (P12), the mice were returned to room air. Maximal retinal neovascularization was observed 5 days after return to room air (P17). After P21, the level of retinal neovascularization was just beginning to regress.

C. Treatment

After mice had been removed from oxygen, antisense oligonucleotides were injected into the vitreous with a Hamilton syringe and a 33 gauge needle (Hamilton Company, Reno, Nev.). The animals were anesthetized for the procedure with Avertin ip. The mice were given a single injection of antisense oligonucleotides (or sense or non-sense controls) at P12 achieving a final concentration of approximately 30–50 µM. The animals were sacrificed at P17 with tribromoethanol ip (0.1 ml/g body weight) and cervical dislocation.

D. Microscopy

The eyes were enucleated, fixed in 4% paraformaldehyde, and embedded in paraffin. Serial sections of the whole eyes were cut sagittally, through the cornea, and parallel to the optic nerve. The sections were stained with hematoxylin and periodic acid-Schiff (PAS) stain. The extent of neovascularization in the treated eyes was determined by counting endothelial cell nuclei extending past the internal limiting membrane into the vitreous. Nuclei from new vessels and vessel profiles could be distinguished from other structures in the retina and counted in cross-section with light microscopy. Additional eyes were sectioned and examined by in situ hybridization to a VEGF probe.

To examine the retinal vasculature using fluorescein-dextran, the mice were perfused with a 50 mg/ml solution of high molecular weight fluorescein-dextran (Sigma Chemical Company, St. Louis, Mo.) in 4% paraformaldehyde. The eyes were enucleated, fixed in paraformaldehyde, and flat-mounted with glycerol-gelatin. The flat-mounted retinas were viewed and photographed by fluorescence microscopy using an Olympus BX60 fluorescence microscope (Olympus America Corp., Bellingham, Mass.).

EXAMPLE 7

Inhibition of VEGF Expression in Human Epidermal Keratinocytes

Normal human epidermal keratinocytes were purchased from CloneticsR (San Diego, Calif.) as grown as recommended in Keratinocyte Growth Medium (KGM) or Keratinocyte Basal Medium (KBM) supplemented with TGF alpha (Gibco BRL, Gaithersburg, Md.). Cells for all experiments were used at passages 2 or 3, and cultured in a humidified incubator with 10% CO2 at 37° C. For antisense treatment, the medium from confluent cells was aspirated and replaced with KBM containing lipofectin (Gibco BRL, Gaithersburg, Md.). Oligonucleotide phosphorothioates described below in TABLE 2 of the appropriate concentration were then added.

TABLE 2

| Oligo | Sequence (5'-3') | SEQ.ID. NO: |
| --- | --- | --- |
| H3 | CACCCAAGACAGCAGAAAG | 1 |
| H3S | CTTTCTGCTGTCTTGGGTG | 21 |
| 5'1bpMM[1] | CTCCCAAGACAGCAGAAAG | 22 |
| 5'2bpMW[2] | CTGCCAAGACAGCAGAAAG | 23 |
| cen4bpMM[3] | CACCCAACTCTCCAGAAAG | 24 |
| 3'1bpMM[4] | CACCCAAGACAGCAGAATG | 25 |
| 3'2bpMM[5] | CACCCAAGACAGCAGATTG | 26 |

[1]-5' one base pair mismatch
[2]-5' two base pair mismatch
[3]-central four base pair mismatch
[4]-3' one base pair mismatch
[5]-3' two base pair mismatch All experiments were performed with 0.5 uM oligodeoxynucleotides, unless otherwise stated. After eight hours, the medium was replaced with KBM in the presence of TGF alpha. The medium was collected at 24 or 48 hours post-TGF alpha addition and analyzed by ELISA as described below. Total RNA was obtained from the cells and analyzed by Northern blot as described below.

96 well plates (Nunc Maxisorp™, Nunc, Denmark) were coated overnight at 4° C. with anti-human VEGF monoclonal antibody (R & D Systems, Minneapolis, Minn.), and blocked for 2 hours with 2% normal human serum. Cell supernatants were added and incubated overnight. Plates were washed 3 times in 0.05% Tween 20 (USB, Cleveland, Ohio)/PBS (Cellgro®, Herndon, Vir.), on a plate washer (Dynatech, Chantilly, Vir.). An affinity purified rabbit anti-human VEGF polyclonal antibody (1.5 µg/ml) was added and allowed to incubate for 2 hours at 37° C. Plates were washed as described above and a 1:10000 dilution of horse radish peroxidase (HRP)-conjugated goat-anti-rabbit IgG secondary antibody, (Kirkegaard and Perry, Gaithersburg, Md.) was added and allowed to incubate for 1 hour. ELISA plates were developed using the TMB Microwell Peroxidase Substrate System (Kirkegaard and Perry, Gaithersburg, Md.) and read on a Ceres 900 microplate reader (Bio-tek Instruments, Winooski, Vt.).

Data from the ELISA shows a specific inhibition of TGFα-induced VEGF to near basal levels by oligonucleotide H3 (SEQ ID NO:1). The control oligonucleotide, H3S sense (SEQ ID NO:21), shows levels equal to cells treated with TGFα alone. These results were confirmed at 24 and 48 hour timepoints.

EXAMPLE 8

Flow Cytometry

A fluorescein moiety was attached to the 5' end of the H3 oligonucleotide phosphorothioate for flow cytometry experiments. For uptake analysis, cells were grown in a 6 well plate in KGM. Two days post-confluence cells were treated in KBM with or without fluorescein-labelled oligonucleotide phosphorothioates in the presence or absence of lipofectin for eight hours. Cells were trypsinized, washed twice with PBS, and analyzed on a flow cytometer (Coulter Epics XL, Hialeah, Fla.) gating on live cells. Fluorescence was monitored at 488 nm with a 525 nm band pass filter.

EXAMPLE 9

Northern Blotting

Total RNA was obtained from cells and analyzed by Northern blot as follows. RNA was prepared using Trizol (Gibco BRL, Gaithersburg, Md.) as per manufacturers directions. Twenty micrograms of total RNA was separated on a 1% formaldehyde denaturing agarose gel (Chomczynski and Makey, (1994) *Anal. Biochem* 221:303–305) transferred to Zeta-Probe® (Biorad, Hercules, Calif.) nylon membrane, and hybridized to a random primer labeled simian VEGF/VPF cDNA probe. A probe for 36B4, a ribosomal associated protein, was used to control for loading. The blot was scanned using a Biorad GS525 Molecular Imager® system. Analysis of the acquired image was performed using the Molecular Analyst software. The signals were quantified by volume analysis (mm2*pixil density). The numbers shown are the ratios of the VEGF/VPF signal divided by the ribosomal protein, 36B4, signal.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of inhibiting vascular endothelial growth factor in tumor cells comprising the step of locally administering to said tumor cells, a therapeutically effective amount of a synthetic oligonucleotide complementary to a human vascular endothelial growth factor target nucleic acid, whereby expression of said vascular endothelial growth factor is inhibited, the oligonucleotide having a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

2. The method of claim 1, wherein the oligonucleotide has a modification selected from the group consisting of an alkylphosphonate, phosphorothioate, phosphorodithioate, phosphate ester, alkylphosphonothioate, phosphoramidate, carbamate, carbonate, phosphate triester, acetamidate, and carboxymethyl ester internucleotide linkage, and a combination thereof.

3. The method of claim 2, wherein the oligonucleotide has at least one phosphorothioate internucleotide linkage.

4. The method of claim 3, wherein the oligonucleotide has phosphorothioate internucleotide linkages.

5. The method of claim 1, wherein the oligonucleotide has 2'-O-alkylated ribonucleotides.

6. The method of claim 5, wherein the oligonucleotide comprises four or five 2'-O-alkylated ribonucleotides at the 5' terminus of the oligonucleotide.

7. The method of claim 5, wherein the oligonucleotide comprises four or five 2'-O-alkylated ribonucleotides at the 3' terminus of the oligonucleotide.

8. The method of claim 1, wherein the oligonucleotide is administered topically.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:1:

CACCCAAGAC AGCAGAAAG                                                    19

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:2:

GCACCCAAGA CAGCAGAAAG                                                   20

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:3:

TGCACCCAAG ACAGCAGAAA G                                                 21

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:4:

ATGCACCCAA GACAGCAGAA AG                                         22

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:5:

AATGCACCCA AGACAGCAGA AAG                                        23

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:6:

CAATGCACCC AAGACAGCAG AAAG                                       24

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:7:

CCAATGCACC CAAGACAGCA GAAAG                                      25

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:8:

TCCAATGCAC CCAAGACAGC AGAAAG                                     26

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:9:

CTCCAATGCA CCCAAGACAG CAGAAAG                                    27

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:10:

GCTCCAATGC ACCCAAGACA GCAGAAAG                                   28

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:11:

GGCTCCAATG CACCCAAGAC AGCAGAAAG                                  29

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:12:

CACCCAAGAC AGCAGAAA                                              18

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:13:

CACCCAAGAC AGCAGAA                                                    17

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:14:

CACCCAAGAC AGCAGA                                                     16

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:15:

CACCCAAGAC AGCAGAAAGT T                                               21

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:16:

CACCCAAGAC AGCAGAAAGT TCAT                                            24

(2) INFORMATION FOR SEQ ID NO:17:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:17:

TCGCGCTCCC TCTCTCCGGC                                               20

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:18:

CATGGTTTCG GAGGGCGTC                                                19

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:19:

CAGCCTGGCT CACCGCCTTG G                                             21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

TCCGAAACCA TGAACTTTCT G                                             21

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

CTTTCTGCTG TCTTGGGTG 19

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:22:

CTCCCAAGAC AGCAGAAAG 19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:23:

CTGCCAAGAC AGCAGAAAG 19

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:24:

CACCCAACTC TCCAGAAAG 19

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA

```
        (iii) HYPOTHETICAL: NO (iv) ANTI-SENSE: YES (xi) SEQUENCE DESCRIPTION: SEQ ID NO:25:

CACCCAAGAC AGCAGAATG                                                19

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:26:

CACCCAAGAC AGCAGATTG                                                19
```